US 8,071,334 B2

(12) United States Patent
Eleouet et al.

(10) Patent No.: US 8,071,334 B2
(45) Date of Patent: Dec. 6, 2011

(54) PREPARATION OF SOLUBLE N-PROTEIN/TRUNCATED P-PROTEIN COMPLEXES OF THE PARAMYXOVIRIDAE FAMILY

(75) Inventors: Jean-Francois Eleouet, Breuillet (FR); Sabine Riffault, Jouy-en-Josas (FR)

(73) Assignee: Institut National de la Recherche Agronomique, Paris (FR)

( * ) Notice: Subject to any disclaimer, the term of this patent is extended or adjusted under 35 U.S.C. 154(b) by 638 days.

(21) Appl. No.: 11/919,542

(22) PCT Filed: Apr. 27, 2006

(86) PCT No.: PCT/FR2006/000949
§ 371 (c)(1),
(2), (4) Date: Oct. 29, 2007

(87) PCT Pub. No.: WO2006/117456
PCT Pub. Date: Nov. 9, 2006

(65) Prior Publication Data
US 2010/0021490 A1    Jan. 28, 2010

(30) Foreign Application Priority Data

Apr. 29, 2005  (FR) ..................................... 05 04426

(51) Int. Cl.
*C12N 15/09*    (2006.01)
*A61K 39/155*    (2006.01)
(52) U.S. Cl. .................. 435/69.3; 424/211.1; 424/212.1
(58) Field of Classification Search ........................ None
See application file for complete search history.

(56) References Cited

FOREIGN PATENT DOCUMENTS

WO    WO 2004087062    10/2004

OTHER PUBLICATIONS

Castagne, et al., "Biochemical characterization of the respiratory syncytial virus P-P and P-N protein complexes and localization of the P protein oligomerization domain" Journal of General Virology, vol. 85, Jun. 2004, pp. 1643-1653.
Slack, et al., "Characterization of the interaction of the human respiratory syncytial virus phosphoprotein and nucleocapsid protein using the two-hybrid system" Virus Research, vol. 55, Jun. 1998, pp. 167-176.
Khattar, et al., "Mapping the domains on the phosphoprotein of bovine respiratory syncytial virus required for N-P and P-L interactions using a minigenome system" Journal of General Virology, vol. 82, Apr. 2001; pp. 775-779.
Choudhary, et al., "Characterization of the oligomerization domain of the phosphoprotein of human parainfluenza virus type 3" Virology, vol. 302, Oct. 2002, pp. 373-382.
Bankamp, et al., "Domains of the measles virus N Protein required for the binding to P protein and self-assembly", Virology, vol. 216, (1996),,pp. 272-277.
Chan, et al., "Mapping of domains responsible for nucleocapsid protein-phosphoprotein interaction of Henipaviruses" Journal of General Virology, Jun. 2004, vol. 85, pp. 1675-1684.
Tawar, Rajiv G., et al., "Crystal Structure of a Nucleocapsid-Like Nucleoprotein-RNA Complex of Respiratory Syncytial Virus", Science, vol. 326, pp. 1279-1283 (Nov. 27, 2009).
Tran, Thi-Lan, et al., "The Nine C-Terminal amino Acids of the Respratory Syncytial Virus Protein P are Necessary and Sufficient for Binding to Ribonucleoprotein Complexes in Which Six Ribonucleotides are Contacted per N Protein Protomer", Journal of General virology, (2007), 88, 196-206.
Mitra-Kaushik, Shibani, et al., "Identification of a cytotoxic T-cell epitope on the recombinant nucleocapsid proteins of rindrpest and peste des petis ruminants viruses presented as assembled nucleocapside", Virology, 279, pp. 210-220 (2001).
Tan, Wen Siang, et al., "Solubility, Immunogenicity and physical properties of the nucleocapsid protein of nipah virus produced in *Escherichia coli*", Journal of Medical Virology, 73, pp. 105-112 (2004).
Curran, Joseph et al., "Paramyxovirus Phosphoproteins Form Homotrimers as Determined by an Epitope Dilution Assay, via Predicted Coiled Coils", Virology, vol. 214, pp. 139-149 (1995).
Rahaman, Abdur et al., "Phosphoprotein of the Rinderpest Virus Forms a Tetramer through a Coiled Coil Region Important for Biological Function", J. Biol. Chem., vol. 279, No. 22, pp. 23606-23614 (2004).
Nishio, Machiko et al., "Human parainfluenza virus type 2 phosphoprotein: mapping of monoclonal antibody epitopes and location of the multimerization domain", J. Gen. Virology, 78, pp. 1303-1308 (1997).
Choudhary, Suresh K. et al., "Characterization of the Oligomerization domain of the Phosphoprotein of Human Parainfluenza Virus Type 3", Virology, 302, pp. 373-382 (2002).

*Primary Examiner* — Stacy B. Chen
(74) *Attorney, Agent, or Firm* — Davidson, Davidson & Kappel, LLC

(57) ABSTRACT

The invention relates to a method for preparation of soluble N-protein/truncated P-protein complex of a virus of the family Paramyxoviridae, complexes prepared thus and the soluble N-proteins which may be isolated from said complexes. The invention further relates to vaccine compositions comprising said N-protein/truncated P-protein complexes or N-proteins from Paramyxoviridae.

22 Claims, 5 Drawing Sheets

SEQUENCE LISTING

```
<160> NUMBER OF SEQ ID NOS: 26

<210> SEQ ID NO 1
<211> LENGTH: 241
<212> TYPE: PRT
<213> ORGANISM: Human respiratory syncytial virus
<220> FEATURE:
<221> NAME/KEY: MISC_FEATURE
<222> LOCATION: (1)..(241)
<223> OTHER INFORMATION: phosphoprotein P (Swissprot P12579)

<400> SEQUENCE: 1

Met Glu Lys Phe Ala Pro Glu Phe His Gly Glu Asp Ala Asn Asn Arg
1               5                   10                  15

Ala Thr Lys Phe Leu Glu Ser Ile Lys Gly Lys Phe Thr Ser Pro Lys
            20                  25                  30

Asp Pro Lys Lys Lys Asp Ser Ile Ile Ser Val Asn Ser Thr Asp Ile
        35                  40                  45

Glu Val Thr Lys Glu Ser Pro Ile Thr Ser Asn Ser Thr Ile Ile Asn
    50                  55                  60

Pro Thr Asn Glu Thr Asp Asp Asn Ala Gly Asn Lys Pro Asn Tyr Gln
65                  70                  75                  80

Arg Lys Pro Leu Val Ser Phe Lys Glu Asp Pro Ile Pro Ser Asp Asn
```

```
            85              90              95
Pro Phe Ser Lys Leu Tyr Lys Glu Thr Ile Glu Thr Phe Asp Asn Asn
            100             105             110

Glu Glu Glu Ser Ser Tyr Ser Tyr Glu Glu Ile Asn Asp Gln Thr Asn
            115             120             125

Asp Asn Ile Thr Ala Arg Leu Asp Arg Ile Asp Glu Lys Leu Ser Glu
            130             135             140

Ile Leu Gly Met Leu His Thr Leu Val Val Ala Ser Ala Gly Pro Thr
145             150             155             160

Ser Ala Arg Asp Gly Ile Arg Asp Ala Met Val Gly Leu Arg Glu Glu
                165             170             175

Met Ile Glu Lys Ile Arg Thr Glu Ala Leu Met Thr Asn Asp Arg Leu
                180             185             190

Glu Ala Met Ala Arg Leu Arg Asn Glu Ser Glu Lys Met Ala Lys
                195             200             205

Asp Thr Ser Asp Glu Val Ser Leu Asn Pro Thr Ser Glu Lys Leu Asn
            210             215             220

Asn Leu Leu Glu Gly Asn Asp Ser Asp Asn Asp Leu Ser Leu Glu Asp
225             230             235             240

Phe

<210> SEQ ID NO 2
<211> LENGTH: 568
<212> TYPE: PRT
<213> ORGANISM: Sendai virus
<220> FEATURE:
<221> NAME/KEY: MISC_FEATURE
<222> LOCATION: (1)..(568)
<223> OTHER INFORMATION: phosphoprotein P (Swissprot P04859)

<400> SEQUENCE: 2

Met Asp Gln Asp Ala Phe Ile Leu Lys Glu Asp Ser Glu Val Glu Arg
1               5               10              15

Glu Ala Pro Gly Gly Arg Glu Ser Leu Ser Asp Val Ile Gly Phe Leu
            20              25              30

Asp Ala Val Leu Ser Ser Glu Pro Thr Asp Ile Gly Gly Asp Arg Ser
        35              40              45

Trp Leu His Asn Thr Ile Asn Thr Pro Gln Gly Pro Gly Ser Ala His
    50              55              60

Arg Ala Lys Ser Glu Gly Glu Gly Val Ser Thr Pro Ser Thr Gln
65              70              75              80

Asp Asn Arg Ser Gly Glu Glu Ser Arg Val Ser Gly Arg Thr Ser Lys
            85              90              95

Pro Glu Ala Glu Ala His Ala Gly Asn Leu Asp Lys Gln Asn Ile His
            100             105             110

Arg Ala Phe Gly Gly Arg Thr Gly Thr Asn Ser Val Ser Gln Asp Leu
            115             120             125

Gly Asp Gly Gly Asp Ser Gly Ile Leu Glu Asn Pro Pro Asn Glu Arg
            130             135             140

Gly Tyr Pro Arg Ser Gly Ile Glu Asp Glu Asn Arg Glu Met Ala Ala
145             150             155             160

His Pro Asp Lys Arg Gly Glu Asp Gln Ala Glu Gly Leu Pro Glu Glu
                165             170             175

Val Arg Gly Gly Thr Ser Leu Pro Asp Glu Gly Glu Gly Gly Ala Ser
                180             185             190

Asn Asn Gly Arg Ser Met Glu Pro Gly Ser Ser His Ser Ala Arg Val
```

```
            195                 200                 205
Thr Gly Val Leu Val Ile Pro Ser Pro Glu Leu Glu Glu Ala Val Leu
210                 215                 220

Arg Arg Asn Lys Arg Arg Pro Thr Asn Ser Gly Ser Lys Pro Leu Thr
225                 230                 235                 240

Pro Ala Thr Val Pro Gly Thr Arg Ser Pro Pro Leu Asn Arg Tyr Asn
                245                 250                 255

Ser Thr Gly Ser Pro Pro Gly Lys Pro Ser Thr Gln Asp Glu His
            260                 265                 270

Ile Asn Ser Gly Asp Thr Pro Ala Val Arg Val Lys Asp Arg Lys Pro
            275                 280                 285

Pro Ile Gly Thr Arg Ser Val Ser Asp Cys Pro Ala Asn Gly Arg Pro
            290                 295                 300

Ile His Pro Gly Leu Glu Ser Asp Ser Thr Lys Lys Gly Ile Gly Glu
305                 310                 315                 320

Asn Thr Ser Ser Met Lys Glu Met Ala Thr Leu Leu Thr Ser Leu Gly
                325                 330                 335

Val Ile Gln Ser Ala Gln Glu Phe Glu Ser Ser Arg Asp Ala Ser Tyr
            340                 345                 350

Val Phe Ala Arg Arg Ala Leu Lys Ser Ala Asn Tyr Ala Glu Met Thr
            355                 360                 365

Phe Asn Val Cys Gly Leu Ile Leu Ser Ala Glu Lys Ser Ser Ala Arg
370                 375                 380

Lys Val Asp Glu Asn Lys Gln Leu Leu Lys Gln Ile Gln Glu Ser Val
385                 390                 395                 400

Glu Ser Phe Arg Asp Ile Tyr Lys Arg Phe Ser Glu Tyr Gln Lys Glu
                405                 410                 415

Gln Asn Ser Leu Leu Met Ser Asn Leu Ser Thr Leu His Ile Ile Thr
            420                 425                 430

Asp Arg Gly Gly Lys Thr Asp Asn Thr Asp Ser Leu Thr Arg Ser Pro
            435                 440                 445

Ser Val Phe Ala Lys Ser Lys Glu Asn Lys Thr Lys Ala Thr Arg Phe
450                 455                 460

Asp Pro Ser Met Glu Thr Leu Glu Asp Met Lys Tyr Lys Pro Asp Leu
465                 470                 475                 480

Ile Arg Glu Asp Glu Phe Arg Asp Glu Ile Arg Asn Pro Val Tyr Gln
                485                 490                 495

Glu Arg Asp Thr Glu Pro Arg Ala Ser Asn Ala Ser Arg Leu Leu Pro
            500                 505                 510

Ser Lys Glu Lys Pro Thr Met His Ser Leu Arg Leu Val Ile Glu Ser
            515                 520                 525

Ser Pro Leu Ser Arg Ala Glu Lys Ala Ala Tyr Val Lys Ser Leu Ser
            530                 535                 540

Lys Cys Lys Thr Asp Gln Glu Val Lys Ala Val Met Glu Leu Val Glu
545                 550                 555                 560

Glu Asp Ile Glu Ser Leu Thr Asn
                565

<210> SEQ ID NO 3
<211> LENGTH: 507
<212> TYPE: PRT
<213> ORGANISM: Measles virus
<220> FEATURE:
<221> NAME/KEY: MISC_FEATURE
<222> LOCATION: (1)..(507)
<223> OTHER INFORMATION: Phsophospr

<400> SEQUENCE: 3

```
Met Ala Glu Glu Gln Ala Arg His Val Lys Asn Gly Leu Glu Cys Ile
1               5                   10                  15

Arg Ala Leu Lys Ala Glu Pro Ile Gly Ser Leu Ala Val Glu Glu Ala
            20                  25                  30

Met Ala Ala Trp Ser Glu Ile Ser Asp Asn Pro Gly Gln Asp Arg Ala
        35                  40                  45

Thr Cys Lys Glu Glu Glu Ala Gly Ser Ser Gly Leu Ser Lys Pro Cys
    50                  55                  60

Leu Ser Ala Ile Gly Ser Thr Glu Gly Gly Ala Pro Arg Ile Arg Gly
65                  70                  75                  80

Gln Gly Ser Gly Glu Ser Asp Asp Ala Glu Thr Leu Gly Ile Pro
                85                  90                  95

Ser Arg Asn Leu Gln Ala Ser Ser Thr Gly Leu Gln Cys Tyr His Val
                100                 105                 110

Tyr Asp His Ser Gly Glu Ala Val Lys Gly Ile Gln Asp Ala Asp Ser
            115                 120                 125

Ile Met Val Gln Ser Gly Leu Asp Gly Asp Ser Thr Leu Ser Gly Gly
130                 135                 140

Asp Asp Glu Ser Glu Asn Ser Asp Val Asp Ile Gly Glu Pro Asp Thr
145                 150                 155                 160

Glu Gly Tyr Ala Ile Thr Asp Arg Gly Ser Ala Pro Ile Ser Met Gly
                165                 170                 175

Phe Arg Ala Ser Asp Val Glu Thr Ala Glu Gly Gly Glu Ile His Glu
            180                 185                 190

Leu Leu Lys Leu Gln Ser Arg Gly Asn Asn Phe Pro Lys Leu Gly Lys
        195                 200                 205

Thr Leu Asn Val Pro Pro Pro Asn Pro Ser Arg Ala Ser Thr Ser
210                 215                 220

Glu Thr Pro Ile Lys Lys Gly Thr Asp Ala Arg Leu Ala Ser Phe Gly
225                 230                 235                 240

Thr Glu Ile Ala Ser Leu Leu Thr Gly Gly Ala Thr Gln Cys Ala Arg
                245                 250                 255

Lys Ser Pro Ser Glu Pro Ser Gly Pro Gly Ala Pro Ala Gly Asn Val
            260                 265                 270

Pro Glu Cys Val Ser Asn Ala Ala Leu Ile Gln Glu Trp Thr Pro Glu
        275                 280                 285

Ser Gly Thr Thr Ile Ser Pro Arg Ser Gln Asn Glu Glu Gly Gly
290                 295                 300

Asp Tyr Tyr Asp Asp Glu Leu Phe Ser Asp Val Gln Asp Ile Lys Thr
305                 310                 315                 320

Ala Leu Ala Lys Ile His Glu Asp Asn Gln Lys Ile Ile Ser Lys Leu
                325                 330                 335

Glu Ser Leu Leu Leu Leu Lys Gly Glu Val Glu Ser Ile Lys Lys Gln
            340                 345                 350

Ile Asn Arg Gln Asn Ile Ser Ile Ser Thr Leu Glu Gly His Leu Ser
        355                 360                 365

Ser Ile Met Ile Ala Ile Pro Gly Leu Gly Lys Asp Pro Asn Asp Pro
370                 375                 380

Thr Ala Asp Val Glu Leu Asn Pro Asp Leu Lys Pro Ile Ile Gly Arg
385                 390                 395                 400

Asp Ser Gly Arg Ala Leu Ala Glu Val Leu Lys Lys Pro Val Ala Ser
                405                 410                 415
```

```
Arg Gln Leu Gln Gly Met Thr Asn Gly Arg Thr Ser Ser Arg Gly Gln
            420                 425                 430

Leu Leu Lys Glu Phe Gln Leu Lys Pro Ile Gly Lys Lys Val Ser Ser
            435                 440                 445

Ala Val Gly Phe Val Pro Asp Thr Gly Pro Ala Ser Arg Ser Val Ile
            450                 455                 460

Arg Ser Ile Ile Lys Ser Ser Arg Leu Glu Glu Asp Arg Lys Arg Tyr
465                 470                 475                 480

Leu Met Thr Leu Leu Asp Asp Ile Lys Gly Ala Asn Asp Leu Ala Lys
            485                 490                 495

Phe His Gln Met Leu Met Lys Ile Ile Met Lys
            500                 505

<210> SEQ ID NO 4
<211> LENGTH: 390
<212> TYPE: PRT
<213> ORGANISM: Mumps virus
<220> FEATURE:
<221> NAME/KEY: MISC_FEATURE
<222> LOCATION: (1)..(390)
<223> OTHER INFORMATION: Phosphoprotein P (Swissprot P19717)

<400> SEQUENCE: 4

Met Asp Gln Phe Ile Lys Gln Asp Glu Thr Gly Asp Leu Ile Glu Thr
1               5                   10                  15

Gly Met Asn Val Ala Asn His Phe Leu Ser Ala Pro Ile Gln Gly Thr
            20                  25                  30

Asn Ser Leu Ser Lys Ala Ser Ile Ile Pro Gly Val Ala Pro Val Leu
            35                  40                  45

Ile Gly Asn Pro Glu Gln Lys Asn Ile Gln His Pro Thr Ala Ser His
    50                  55                  60

Gln Gly Ser Lys Ser Lys Gly Ser Gly Ser Gly Val Arg Ser Ile Ile
65                  70                  75                  80

Val Pro Pro Ser Glu Ala Ser Asn Gly Gly Thr Gln Ile Pro Glu Pro
                85                  90                  95

Leu Phe Ala Gln Thr Gly Gln Gly Gly Ile Val Thr Thr Val Tyr Gln
            100                 105                 110

Asp Pro Thr Ile Gln Pro Thr Gly Ser Tyr Arg Ser Val Glu Leu Ala
            115                 120                 125

Lys Ile Gly Lys Glu Arg Met Ile Asn Arg Phe Val Glu Lys Pro Arg
    130                 135                 140

Thr Ser Thr Pro Val Thr Glu Phe Lys Arg Gly Ala Gly Ser Arg Ala
145                 150                 155                 160

Gln Gly Gln Thr Ile Gln Glu Glu Gly Ile Asp Gly Asn Gly Ala Ser
                165                 170                 175

Ala Gly Ser Lys Glu Arg Ser Gly Ser Leu Ser Gly Ala Thr Leu Tyr
            180                 185                 190

Ala His Leu Ser Leu Pro Gln Gln Asp Ser Thr Pro Ala Asn Val Gly
            195                 200                 205

Ile Ala Pro Gln Ser Ala Ile Ser Ala Asn Glu Ile Met Asp Leu Leu
    210                 215                 220

Arg Gly Met Asp Ala Arg Leu Gln His Leu Glu Gln Lys Val Asp Lys
225                 230                 235                 240

Val Leu Ala Gln Gly Ser Met Val Thr Gln Ile Lys Asn Glu Leu Ser
                245                 250                 255

Thr Val Lys Thr Thr Leu Ala Thr Ile Glu Gly Met Met Ala Thr Val
```

```
                    260                 265                 270
Lys Ile Met Asp Pro Gly Asn Pro Thr Gly Val Pro Val Asp Glu Leu
            275                 280                 285

Arg Arg Ser Phe Ser Asp His Val Thr Ile Val Ser Gly Pro Gly Asp
        290                 295                 300

Val Pro Phe Ser Ser Ser Glu Glu Pro Thr Leu Tyr Leu Asp Glu Leu
305                 310                 315                 320

Ala Arg Pro Val Ser Lys Pro Arg Pro Ala Lys Gln Thr Lys Pro Gln
            325                 330                 335

Pro Val Lys Asp Leu Ala Gly Arg Lys Val Met Ile Thr Lys Met Ile
        340                 345                 350

Thr Asp Cys Val Ala Asn Pro Gln Met Lys Gln Ala Phe Glu Gln Arg
    355                 360                 365

Leu Ala Lys Ala Ser Thr Glu Asp Ala Leu Asn Asp Ile Lys Lys Asp
    370                 375                 380

Ile Ile Arg Ser Ala Ile
385                 390

<210> SEQ ID NO 5
<211> LENGTH: 294
<212> TYPE: PRT
<213> ORGANISM: Human Metapneumovirus
<220> FEATURE:
<221> NAME/KEY: MISC_FEATURE
<222> LOCATION: (1)..(517)
<223> OTHER INFORMATION: phosphoprotein P (Swissprot Q91KZ5)

<400> SEQUENCE: 5

Met Ser Phe Pro Glu Gly Lys Asp Ile Leu Phe Met Gly Asn Glu Ala
1               5                   10                  15

Ala Lys Leu Ala Glu Ala Phe Gln Lys Ser Leu Arg Lys Pro Gly His
            20                  25                  30

Lys Arg Ser Gln Ser Ile Ile Gly Glu Lys Val Asn Thr Val Ser Glu
        35                  40                  45

Thr Leu Glu Leu Pro Thr Ile Ser Arg Pro Ala Lys Pro Thr Ile Pro
    50                  55                  60

Ser Glu Pro Lys Leu Ala Trp Thr Asp Lys Gly Gly Ala Thr Lys Thr
65                  70                  75                  80

Glu Ile Lys Gln Ala Ile Lys Val Met Asp Pro Ile Glu Glu Glu Glu
                85                  90                  95

Ser Thr Glu Lys Lys Val Leu Pro Ser Ser Asp Gly Lys Thr Pro Ala
            100                 105                 110

Glu Lys Lys Leu Lys Pro Ser Thr Asn Thr Lys Lys Lys Val Ser Phe
        115                 120                 125

Thr Pro Asn Glu Pro Gly Lys Tyr Thr Lys Leu Glu Lys Asp Ala Leu
    130                 135                 140

Asp Leu Leu Ser Asp Asn Glu Glu Glu Asp Ala Glu Ser Ser Ile Leu
145                 150                 155                 160

Thr Phe Glu Glu Arg Asp Thr Ser Ser Leu Ser Ile Glu Ala Arg Leu
                165                 170                 175

Glu Ser Ile Glu Glu Lys Leu Ser Met Ile Leu Gly Leu Leu Arg Thr
            180                 185                 190

Leu Asn Ile Ala Thr Ala Gly Pro Thr Ala Ala Arg Asp Gly Ile Arg
        195                 200                 205

Asp Ala Met Ile Gly Val Arg Glu Glu Leu Ile Ala Asp Ile Ile Lys
    210                 215                 220
```

-continued

```
Glu Ala Lys Gly Lys Ala Ala Glu Met Met Glu Glu Met Ser Gln
225                 230                 235                 240

Arg Ser Lys Ile Gly Asn Gly Ser Val Lys Leu Thr Glu Lys Ala Lys
                245                 250                 255

Glu Leu Asn Lys Ile Val Glu Asp Glu Ser Thr Ser Gly Glu Ser Glu
            260                 265                 270

Glu Glu Glu Glu Pro Lys Asp Thr Gln Asp Asn Ser Gln Glu Asp Asp
        275                 280                 285

Ile Tyr Gln Leu Ile Met
        290

<210> SEQ ID NO 6
<211> LENGTH: 391
<212> TYPE: PRT
<213> ORGANISM: Human respiratory syncytial virus
<220> FEATURE:
<221> NAME/KEY: MISC_FEATURE
<222> LOCATION: (1)..(391)
<223> OTHER INFORMATION: nucleocapsid protein (strain LONG)

<400> SEQUENCE: 6

Met Ala Leu Ser Lys Val Lys Leu Asn Asp Thr Leu Asn Lys Asp Gln
1               5                   10                  15

Leu Leu Ser Ser Ser Lys Tyr Thr Ile Gln Arg Ser Thr Gly Asp Ser
            20                  25                  30

Ile Asp Thr Pro Asn Tyr Asp Val Gln Lys His Ile Asn Lys Leu Cys
        35                  40                  45

Gly Met Leu Leu Ile Thr Glu Asp Ala Asn His Lys Phe Thr Gly Leu
    50                  55                  60

Ile Gly Met Leu Tyr Ala Met Ser Arg Leu Gly Arg Glu Asp Thr Ile
65                  70                  75                  80

Lys Ile Leu Arg Asp Ala Gly Tyr His Val Lys Ala Asn Gly Val Asp
                85                  90                  95

Val Thr Thr His Arg Gln Asp Ile Asn Gly Lys Glu Met Lys Phe Glu
            100                 105                 110

Val Leu Thr Leu Ser Ser Leu Thr Thr Glu Ile Gln Ile Asn Ile Glu
        115                 120                 125

Ile Glu Ser Arg Lys Ser Tyr Lys Lys Met Leu Lys Glu Met Gly Glu
    130                 135                 140

Val Ala Pro Glu Tyr Arg His Asp Ser Pro Asp Cys Gly Met Ile Ile
145                 150                 155                 160

Leu Cys Ile Ala Ala Leu Val Ile Thr Lys Leu Ala Ala Gly Asp Arg
                165                 170                 175

Ser Gly Leu Thr Ala Val Ile Arg Arg Ala Asn Asn Val Leu Lys Asn
            180                 185                 190

Glu Met Lys Arg Tyr Lys Gly Leu Leu Pro Lys Asp Ile Ala Asn Ser
        195                 200                 205

Phe Tyr Glu Val Phe Glu Lys Tyr Pro His Phe Ile Asp Val Phe Val
    210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
            260                 265                 270

Gly His Ala Ser Val Gln Ala Glu Met Glu Gln Val Val Glu Val Tyr
        275                 280                 285
```

```
Glu Tyr Ala Gln Lys Leu Gly Gly Glu Ala Gly Phe Tyr His Ile Leu
    290                 295                 300

Asn Asn Pro Lys Ala Ser Leu Leu Ser Leu Thr Gln Phe Pro His Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
                340                 345                 350

Tyr Ala Glu Gln Leu Lys Glu Asn Gly Val Ile Asn Tyr Ser Val Leu
            355                 360                 365

Asp Leu Thr Ala Glu Glu Leu Glu Ala Ile Lys His Gln Leu Asn Pro
    370                 375                 380

Lys Asp Asn Asp Val Glu Leu
385                 390

<210> SEQ ID NO 7
<211> LENGTH: 524
<212> TYPE: PRT
<213> ORGANISM: Sendai virus
<220> FEATURE:
<221> NAME/KEY: MISC_FEATURE
<222> LOCATION: (1)..(524)
<223> OTHER INFORMATION: nucleocapsid protein (Swissprot Q9DUE3)

<400> SEQUENCE: 7

Met Ala Gly Leu Leu Ser Thr Phe Asp Thr Phe Ser Ser Arg Arg Ser
1               5                   10                  15

Glu Ser Ile Asn Lys Ser Gly Gly Gly Ala Val Ile Pro Gly Gln Arg
            20                  25                  30

Ser Thr Val Ser Val Phe Val Leu Gly Pro Ser Val Thr Asp Asp Ala
        35                  40                  45

Asp Lys Leu Phe Ile Ala Thr Thr Phe Leu Ala His Ser Leu Asp Thr
    50                  55                  60

Asp Lys Gln His Ser Gln Arg Gly Gly Phe Leu Val Ser Leu Leu Ala
65                  70                  75                  80

Met Ala Tyr Ser Ser Pro Glu Leu Tyr Leu Thr Thr Asn Gly Val Asn
                85                  90                  95

Ala Asp Val Lys Tyr Val Ile Tyr Asn Ile Glu Lys Asp Pro Lys Arg
            100                 105                 110

Thr Lys Thr Asp Gly Phe Ile Val Lys Thr Arg Asp Met Glu Tyr Glu
        115                 120                 125

Arg Thr Thr Glu Trp Leu Phe Gly Pro Met Val Asn Lys Ser Pro Leu
    130                 135                 140

Phe Gln Gly Gln Arg Asp Ala Ala Asp Pro Asp Thr Leu Leu Gln Ile
145                 150                 155                 160

Tyr Gly Tyr Pro Ala Cys Leu Gly Ala Ile Ile Val Gln Val Trp Ile
                165                 170                 175

Val Leu Val Lys Ala Ile Thr Ser Ser Ala Gly Leu Arg Lys Gly Phe
            180                 185                 190

Phe Asn Arg Leu Glu Ala Phe Arg Gln Asp Gly Thr Val Lys Gly Ala
        195                 200                 205

Leu Val Phe Thr Gly Glu Thr Val Glu Gly Ile Gly Ser Val Met Arg
    210                 215                 220

Ser Gln Gln Ser Leu Val Ser Leu Met Val Glu Thr Leu Val Thr Met
225                 230                 235                 240

Asn Thr Ala Arg Ser Asp Leu Thr Thr Leu Glu Lys Asn Ile Gln Ile
```

```
                245                 250                 255

Val Gly Asn Tyr Ile Arg Asp Ala Gly Leu Ala Ser Phe Met Asn Thr
            260                 265                 270

Ile Lys Tyr Gly Val Glu Thr Lys Met Ala Ala Leu Thr Leu Ser Asn
        275                 280                 285

Leu Arg Pro Asp Ile Asn Lys Leu Arg Ser Leu Ile Asp Thr Tyr Leu
    290                 295                 300

Ser Lys Gly Pro Arg Ala Pro Phe Ile Cys Ile Leu Lys Asp Pro Val
305                 310                 315                 320

His Gly Glu Phe Ala Pro Gly Asn Tyr Pro Ala Leu Trp Ser Tyr Ala
                325                 330                 335

Met Gly Val Ala Val Val Gln Asn Lys Ala Met Gln Gln Tyr Val Thr
            340                 345                 350

Gly Arg Thr Tyr Leu Asp Met Glu Met Phe Leu Leu Gly Gln Ala Val
        355                 360                 365

Ala Lys Asp Ala Glu Ser Lys Ile Ser Ser Ala Leu Glu Asp Glu Leu
    370                 375                 380

Gly Val Thr Asp Thr Ala Lys Glu Arg Leu Arg His His Leu Ala Asn
385                 390                 395                 400

Leu Ser Gly Gly Asp Gly Ala Tyr His Lys Pro Thr Gly Gly Gly Ala
                405                 410                 415

Ile Glu Val Ala Leu Asp Asn Ala Asp Ile Asp Leu Glu Pro Glu Ala
            420                 425                 430

His Thr Asp Gln Asp Ala Arg Gly Trp Gly Gly Asp Ser Gly Asp Arg
        435                 440                 445

Trp Ala Arg Ser Thr Ser Ser Gly His Phe Ile Thr Leu His Gly Ala
    450                 455                 460

Glu Arg Leu Glu Glu Glu Thr Asn Asp Glu Asp Val Ser Asp Ile Glu
465                 470                 475                 480

Arg Arg Ile Ala Arg Arg Leu Ala Glu Arg Arg Gln Glu Asp Ala Thr
                485                 490                 495

Thr His Glu Asp Glu Gly Arg Asn Asn Gly Val Asp His Asp Glu Glu
            500                 505                 510

Asp Asp Ala Ala Ala Ala Ala Gly Met Gly Gly Ile
        515                 520

<210> SEQ ID NO 8
<211> LENGTH: 525
<212> TYPE: PRT
<213> ORGANISM: Measles virus
<220> FEATURE:
<221> NAME/KEY: MISC_FEATURE
<222> LOCATION: (1)..(525)
<223> OTHER INFORMATION: Nucleocapsid protein (Swissprot Q89933)

<400> SEQUENCE: 8

Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80
```

-continued

```
Val Glu Ser Pro Gly Gln Leu Ile Gln Arg Ile Thr Asp Asp Pro Asp
                 85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125

Gln Tyr Phe Ser His Asp Asp Pro Ile Ser Ser Asp Gln Ser Arg Phe
    130                 135                 140

Gly Trp Phe Glu Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
            180                 185                 190

Leu Arg Arg Trp Ile Lys Tyr Thr Gln Gln Arg Arg Val Val Gly Glu
        195                 200                 205

Phe Arg Leu Glu Arg Lys Trp Leu Asp Val Val Arg Asn Arg Ile Ala
    210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
                245                 250                 255

Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
    290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
    370                 375                 380

Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
                405                 410                 415

Val Ser Phe Leu His Gly Asp Gln Ser Glu Asn Glu Leu Pro Arg Leu
            420                 425                 430

Gly Gly Lys Glu Asp Arg Arg Val Lys Gln Ser Arg Gly Glu Ala Arg
        435                 440                 445

Glu Ser Tyr Arg Glu Thr Gly Pro Ser Arg Ala Ser Asp Ala Arg Ala
    450                 455                 460

Ala His Leu Pro Thr Gly Thr Pro Leu Asp Ile Asp Thr Ala Ser Glu
465                 470                 475                 480

Ser Ser Gln Asp Pro Gln Asp Ser Arg Arg Ser Ala Asp Ala Leu Leu
                485                 490                 495

Arg Leu Gln Ala Met Ala Gly Ile Ser Glu Glu Gln Gly Ser Asp Thr
            500                 505                 510
```

Asp Thr Pro Ile Val Tyr Asn Asp Arg Asn Leu Leu Asp
        515                 520                 525

<210> SEQ ID NO 9
<211> LENGTH: 553
<212> TYPE: PRT
<213> ORGANISM: Mumps virus
<220> FEATURE:
<221> NAME/KEY: MISC_FEATURE
<222> LOCATION: (1)..(553)
<223> OTHER INFORMATION: Nucleocapsid protein (Swissprot P21277)

<400> SEQUENCE: 9

Met Ser Ser Val Leu Lys Ala Phe Glu Arg Phe Thr Ile Glu Gln Glu
1               5                   10                  15

Leu Gln Asp Arg Gly Glu Glu Gly Ser Ile Pro Pro Glu Thr Leu Lys
            20                  25                  30

Ser Ala Val Lys Val Phe Val Ile Asn Thr Pro Asn Pro Thr Thr Arg
        35                  40                  45

Tyr Gln Met Leu Asn Phe Cys Leu Arg Ile Ile Cys Ser Gln Asn Arg
    50                  55                  60

Arg Ala Ser His Arg Val Gly Ala Leu Ile Ala Leu Phe Ser Leu Pro
65                  70                  75                  80

Ser Ala Gly Met Gln Asn His Ile Arg Leu Ala Asp Arg Ser Pro Glu
                85                  90                  95

Ala Gln Ile Glu Arg Cys Glu Ile Asp Gly Phe Glu Pro Gly Thr Tyr
            100                 105                 110

Arg Leu Ile Pro Asn Ala Arg Ala Asn Leu Thr Ala Asn Glu Ile Ala
        115                 120                 125

Ala Tyr Ala Leu Leu Ala Asp Asp Leu Pro Pro Thr Ile Asn Asn Gly
    130                 135                 140

Thr Pro Tyr Val His Ala Asp Val Glu Leu Gln Pro Cys Asp Glu Ile
145                 150                 155                 160

Glu Gln Phe Leu Asp Arg Cys Tyr Ser Val Leu Ile Gln Ala Trp Val
                165                 170                 175

Met Val Cys Lys Cys Met Thr Ala Tyr Asp Gln Pro Ala Gly Ser Ala
            180                 185                 190

Asp Arg Arg Phe Ala Lys Tyr Gln Gln Gln Gly Arg Leu Glu Ala Arg
        195                 200                 205

Tyr Met Leu Gln Pro Glu Ala Gln Arg Leu Ile Gln Thr Ala Ile Arg
    210                 215                 220

Lys Ser Leu Val Val Arg Gln Tyr Leu Thr Phe Glu Leu Gln Leu Ala
225                 230                 235                 240

Arg Arg Gln Gly Leu Leu Ser Asn Arg Tyr Tyr Ala Met Val Gly Asp
                245                 250                 255

Ile Gly Lys Tyr Ile Glu Asn Ser Gly Leu Thr Ala Phe Phe Leu Thr
            260                 265                 270

Leu Lys Tyr Ala Leu Gly Thr Lys Trp Ser Pro Leu Ser Leu Ala Ala
        275                 280                 285

Phe Thr Gly Glu Leu Thr Lys Leu Arg Ser Leu Met Met Leu Tyr Arg
    290                 295                 300

Asp Ile Gly Glu Gln Ala Arg Tyr Leu Ala Leu Leu Glu Ala Pro Gln
305                 310                 315                 320

Ile Met Asp Phe Ala Pro Gly Gly Tyr Pro Leu Ile Phe Ser Tyr Ala
                325                 330                 335

Met Gly Val Gly Ser Val Leu Asp Val Gln Met Arg Asn Tyr Thr Tyr

```
        340                 345                 350

Ala Arg Pro Phe Leu Asn Gly Tyr Tyr Phe Gln Ile Gly Val Glu Thr
        355                 360                 365

Ala Arg Arg Gln Gln Gly Thr Val Asp Asn Arg Val Ala Asp Asp Leu
    370                 375                 380

Gly Leu Thr Pro Glu Gln Arg Asn Glu Val Thr Gln Leu Val Asp Arg
385                 390                 395                 400
Leu Ala Arg Gly Arg Gly Ala Gly Ile Pro Gly Gly Pro Val Asn Pro
                405                 410                 415

Phe Val Pro Pro Val Gln Gln Gln Gln Pro Ala Ala Val Tyr Ala Asp
            420                 425                 430

Ile Pro Ala Leu Glu Glu Ser Asp Asp Asp Gly Asp Glu Asp Gly Gly
        435                 440                 445

Ala Gly Phe Gln Asn Gly Val Gln Val Pro Ala Val Arg Gln Gly Gly
    450                 455                 460

Gln Thr Asp Phe Arg Ala Gln Pro Leu Gln Asp Pro Ile Gln Ala Gln
465                 470                 475                 480
Leu Phe Met Pro Leu Tyr Pro Gln Val Ser Asn Ile Pro Asn Asn Arg
                485                 490                 495
Ile Ile Arg Ser Ile Ala Ser Gly Gly Trp Lys Thr Lys Ile Tyr Tyr
            500                 505                 510

Asp Thr Thr Arg Met Val Ile Leu Asn Lys Met Gln Gly Ala Asn Thr
        515                 520                 525

Glu Thr Leu Ser Gln Thr Ile Pro Ile Lys Thr His Ser Cys Lys Trp
    530                 535                 540

Ala Thr Gly Met Ser Lys Ser Leu Thr
545                 550

<210> SEQ ID NO 10
<211> LENGTH: 394
<212> TYPE: PRT
<213> ORGANISM: Human Metapneumovirus
<220> FEATURE:
<221> NAME/KEY: MISC_FEATURE
<222> LOCATION: (1)..(394)
<223> OTHER INFORMATION: nucleocapsid protein N (Swissprot Q91F57)

<400> SEQUENCE: 10

Met Ser Leu Gln Gly Ile His Leu Ser Asp Leu Ser Tyr Lys His Ala
1               5                   10                  15

Ile Leu Lys Glu Ser Gln Tyr Thr Ile Lys Arg Asp Val Gly Thr Thr
            20                  25                  30

Thr Ala Val Thr Pro Ser Ser Leu Gln Gln Glu Ile Thr Leu Leu Cys
        35                  40                  45

Gly Glu Ile Leu Tyr Ala Lys His Ala Asp Tyr Lys Tyr Ala Ala Glu
    50                  55                  60

Ile Gly Ile Gln Tyr Ile Ser Thr Ala Leu Gly Ser Glu Arg Val Gln
65                  70                  75                  80

Gln Ile Leu Arg Asn Ser Gly Ser Glu Val Gln Val Val Leu Thr Arg
                85                  90                  95

Thr Tyr Ser Leu Gly Lys Ile Lys Asn Asn Lys Gly Glu Asp Leu Gln
            100                 105                 110

Met Leu Asp Ile His Gly Val Glu Lys Ser Trp Val Glu Glu Ile Asp
        115                 120                 125

Lys Glu Ala Arg Lys Thr Met Ala Thr Leu Leu Lys Glu Ser Ser Gly
    130                 135                 140
```

```
Asn Ile Pro Gln Asn Gln Arg Pro Ser Ala Pro Asp Thr Pro Ile Ile
145                 150                 155                 160
Leu Leu Cys Val Gly Ala Leu Ile Phe Thr Lys Leu Ala Ser Thr Ile
                165                 170                 175
Glu Val Gly Leu Glu Thr Thr Val Arg Arg Ala Asn Arg Val Leu Ser
            180                 185                 190
Asp Ala Leu Lys Arg Tyr Pro Arg Met Asp Ile Pro Lys Ile Ala Arg
        195                 200                 205
Ser Phe Tyr Asp Leu Phe Glu Gln Lys Val Tyr His Arg Ser Leu Phe
    210                 215                 220
Ile Glu Tyr Gly Lys Ala Leu Gly Ser Ser Thr Gly Ser Lys Ala
225                 230                 235                 240
Glu Ser Leu Phe Val Asn Ile Phe Met Gln Ala Tyr Gly Ala Gly Gln
                245                 250                 255
Thr Met Leu Arg Trp Gly Val Ile Ala Arg Ser Ser Asn Asn Ile Met
            260                 265                 270
Leu Gly His Val Ser Val Gln Ala Glu Leu Lys Gln Val Thr Glu Val
        275                 280                 285
Tyr Asp Leu Val Arg Glu Met Gly Pro Glu Ser Gly Leu Leu His Leu
    290                 295                 300
Arg Gln Ser Pro Lys Ala Gly Leu Leu Ser Leu Ala Asn Cys Pro Asn
305                 310                 315                 320
Phe Ala Ser Val Val Leu Gly Asn Ala Ser Gly Leu Gly Ile Ile Gly
                325                 330                 335
Met Tyr Arg Gly Arg Val Pro Asn Thr Glu Leu Phe Ser Ala Ala Glu
            340                 345                 350
Ser Tyr Ala Lys Ser Leu Lys Glu Ser Asn Lys Ile Asn Phe Ser Ser
        355                 360                 365
Leu Gly Leu Thr Asp Glu Glu Lys Glu Ala Ala Glu His Phe Leu Asn
    370                 375                 380
Val Ser Asp Asp Ser Gln Asn Asp Tyr Glu
385                 390

<210> SEQ ID NO 11
<211> LENGTH: 31
<212> TYPE: DNA
<213> ORGANISM: Artificial sequence
<220> FEATURE:
<223> OTHER INFORMATION: primer

<400> SEQUENCE: 11
gagggatcca tcatggaaaa gtttgctcct g                              31

<210> SEQ ID NO 12
<211> LENGTH: 27
<212> TYPE: DNA
<213> ORGANISM: Artificial sequence
<220> FEATURE:
<223> OTHER INFORMATION: primer

<400> SEQUENCE: 12
ctgttggtgt tgtgtgttga agtgcag                                   27

<210> SEQ ID NO 13
<211> LENGTH: 31
<212> TYPE: DNA
<213> ORGANISM: Artificial sequence
<220> FEATURE:
<223> OTHER INFORMATION: primer
```

```
<400> SEQUENCE: 13
gagggatcct ctgctaggga tggtataaga g                              31

<210> SEQ ID NO 14
<211> LENGTH: 36
<212> TYPE: DNA
<213> ORGANISM: Artificial sequence
<220> FEATURE:
<223> OTHER INFORMATION: primer

<400> SEQUENCE: 14
gagggatcca aaatcagaac tgaagcatta atgacc                         36

<210> SEQ ID NO 15
<211> LENGTH: 34
<212> TYPE: DNA
<213> ORGANISM: Artificial sequence
<220> FEATURE:
<223> OTHER INFORMATION: primer

<400> SEQUENCE: 15
gagggatccg aggaaagtga aaagatggca aaag                           34

<210> SEQ ID NO 16
<211> LENGTH: 31
<212> TYPE: DNA
<213> ORGANISM: Artificial sequence
<220> FEATURE:
<223> OTHER INFORMATION: primer

<400> SEQUENCE: 16
gagggatccg agaaattgaa caacctgttg g                              31

<210> SEQ ID NO 17
<211> LENGTH: 44
<212> TYPE: DNA
<213> ORGANISM: Artificial sequence
<220> FEATURE:
<223> OTHER INFORMATION: primer

<400> SEQUENCE: 17
gatccaatga tagtgacaat gatctatcac ttgaagattt ctga                44

<210> SEQ ID NO 18
<211> LENGTH: 40
<212> TYPE: DNA
<213> ORGANISM: Artificial sequence
<220> FEATURE:
<223> OTHER INFORMATION: primer

<400> SEQUENCE: 18
tcagaaatct tcaagtgata gatcattgtc actatcattg                     40

<210> SEQ ID NO 19
<211> LENGTH: 33
<212> TYPE: DNA
<213> ORGANISM: Artificial sequence
<220> FEATURE:
<223> OTHER INFORMATION: primer

<400> SEQUENCE: 19
gagggatcca tggctcttag caaagtcaag ttg                            33

<210> SEQ ID NO 20
<211> LENGTH: 32
<212> TYPE: DNA
```

<213> ORGANISM: Artificial sequence
<220> FEATURE:
<223> OTHER INFORMATION: primer

<400> SEQUENCE: 20
ttaactcaaa gctctacatc attatctttt gg                          32

<210> SEQ ID NO 21
<211> LENGTH: 41
<212> TYPE: DNA
<213> ORGANISM: Artificial sequence
<220> FEATURE:
<223> OTHER INFORMATION: primer

<400> SEQUENCE: 21
gatccgatag tgacaatgat ctatcacttg aagatttctg a                41

<210> SEQ ID NO 22
<211> LENGTH: 37
<212> TYPE: DNA
<213> ORGANISM: Artificial sequence
<220> FEATURE:
<223> OTHER INFORMATION: primer

<400> SEQUENCE: 22
tcagaaatct tcaagtgata gatcattgtc actatcg                    37

<210> SEQ ID NO 23
<211> LENGTH: 241
<212> TYPE: PRT
<213> ORGANISM: Bovine respiratory syncytial virus
<220> FEATURE:
<221> NAME/KEY: MISC_FEATURE
<222> LOCATION: (1)..(241)
<223> OTHER INFORMATION: phopshoprotein P (strain A51908, Swissprot
      P33454)

<400> SEQUENCE: 23

```
Met Glu Lys Phe Ala Pro Glu Phe His Gly Glu Asp Ala Asn Thr Lys
1               5                   10                  15

Ala Thr Lys Phe Leu Glu Ser Leu Lys Gly Lys Phe Thr Ser Ser Lys
            20                  25                  30

Asp Ser Arg Lys Lys Asp Ser Ile Ile Ser Val Asn Ser Ile Asp Ile
        35                  40                  45

Glu Leu Pro Lys Glu Ser Pro Ile Thr Ser Thr Asn His Asn Ile Asn
    50                  55                  60

Gln Pro Ser Glu Ile Asn Asp Thr Ile Ala Ala Asn Gln Val His Ile
65                  70                  75                  80

Arg Lys Pro Leu Val Ser Phe Lys Glu Glu Leu Pro Ser Ser Glu Asn
                85                  90                  95

Pro Phe Thr Lys Leu Tyr Lys Glu Thr Ile Glu Thr Phe Asp Asn Asn
            100                 105                 110

Glu Glu Glu Ser Ser Tyr Ser Tyr Asp Glu Ile Asn Asp Gln Thr Asn
        115                 120                 125

Asp Asn Ile Thr Ala Arg Leu Asp Arg Ile Asp Glu Lys Leu Ser Glu
    130                 135                 140

Ile Ile Gly Met Leu His Thr Leu Val Val Ala Ser Ala Gly Pro Thr
145                 150                 155                 160

Ala Ala Arg Asp Gly Ile Arg Asp Ala Met Val Gly Leu Arg Glu Glu
                165                 170                 175

Met Ile Glu Lys Ile Arg Ser Glu Ala Leu Met Thr Asn Asp Arg Leu
            180                 185                 190
```

-continued

```
Glu Ala Met Ala Arg Leu Arg Asp Glu Glu Ser Glu Lys Met Thr Lys
            195                 200                 205

Asp Thr Ser Asp Glu Val Lys Leu Thr Pro Thr Ser Glu Lys Leu Asn
        210                 215                 220

Met Val Leu Glu Asp Glu Ser Ser Asp Asn Asp Leu Ser Leu Glu Asp
225                 230                 235                 240

Phe

<210> SEQ ID NO 24
<211> LENGTH: 391
<212> TYPE: PRT
<213> ORGANISM: Bovine respiratory syncytial virus
<220> FEATURE:
<221> NAME/KEY: MISC_FEATURE
<222> LOCATION: (1)..(391)
<223> OTHER INFORMATION: nucleocapsid protein N (strain 391-2, Swissprot
      P35943)

<400> SEQUENCE: 24

Met Ala Leu Ser Lys Val Lys Leu Asn Asp Thr Phe Asn Lys Asp Gln
1               5                   10                  15

Leu Leu Ser Thr Ser Lys Tyr Thr Ile Gln Arg Ser Thr Gly Asp Asn
            20                  25                  30

Ile Asp Ile Pro Asn Tyr Asp Val Gln Lys His Leu Asn Lys Leu Cys
        35                  40                  45

Gly Met Leu Leu Ile Thr Glu Asp Ala Asn His Lys Phe Thr Gly Leu
    50                  55                  60

Ile Gly Met Leu Tyr Ala Met Ser Arg Leu Gly Arg Glu Asp Thr Leu
65                  70                  75                  80

Lys Ile Leu Lys Asp Ala Gly Tyr Gln Val Arg Ala Asn Gly Val Asp
                85                  90                  95

Val Ile Thr His Arg Gln Asp Val Asn Gly Lys Glu Met Lys Phe Glu
            100                 105                 110

Val Leu Thr Leu Val Ser Leu Thr Ser Glu Val Gln Gly Asn Ile Glu
        115                 120                 125

Ile Glu Ser Arg Lys Ser Tyr Lys Lys Met Leu Lys Glu Met Gly Glu
    130                 135                 140

Val Ala Pro Glu Tyr Arg His Asp Phe Pro Asp Cys Gly Met Ile Val
145                 150                 155                 160

Leu Cys Val Ala Ala Leu Val Ile Thr Lys Leu Ala Ala Gly Asp Arg
                165                 170                 175

Ser Gly Leu Thr Ala Val Ile Arg Arg Ala Asn Asn Val Leu Arg Asn
            180                 185                 190

Glu Met Lys Arg Tyr Lys Gly Leu Ile Pro Lys Asp Ile Ala Asn Ser
        195                 200                 205

Phe Tyr Glu Val Phe Glu Lys Tyr Pro His Tyr Ile Asp Val Phe Val
    210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
            260                 265                 270

Gly His Ala Ser Val Gln Ala Glu Met Glu Gln Val Val Glu Val Tyr
        275                 280                 285

Glu Tyr Ala Gln Lys Leu Gly Gly Glu Ala Gly Phe Tyr His Ile Leu
```

```
                    290                 295                 300

Asn Asn Pro Lys Ala Ser Leu Leu Ser Leu Thr Gln Phe Pro Asn Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
            340                 345                 350

Tyr Ala Glu Gln Leu Lys Glu Asn Gly Val Ile Asn Tyr Ser Val Leu
        355                 360                 365

Asp Leu Thr Thr Glu Glu Leu Glu Ala Ile Lys Asn Gln Leu Asn Pro
370                 375                 380

Lys Asp Asn Asp Val Glu Leu
385                 390

<210> SEQ ID NO 25
<211> LENGTH: 294
<212> TYPE: PRT
<213> ORGANISM: Human metapneumovirus
<220> FEATURE:
<221> NAME/KEY: MISC_FEATURE
<222> LOCATION: (1)..(294)
<223> OTHER INFORMATION: phosphoprotein P (Swissprot Q91KZ5)

<400> SEQUENCE: 25

Met Ser Phe Pro Glu Gly Lys Asp Ile Leu Phe Met Gly Asn Glu Ala
1               5                   10                  15

Ala Lys Leu Ala Glu Ala Phe Gln Lys Ser Leu Arg Lys Pro Gly His
            20                  25                  30

Lys Arg Ser Gln Ser Ile Ile Gly Glu Lys Val Asn Thr Val Ser Glu
        35                  40                  45

Thr Leu Glu Leu Pro Thr Ile Ser Arg Pro Ala Lys Pro Thr Ile Pro
    50                  55                  60

Ser Glu Pro Lys Leu Ala Trp Thr Asp Lys Gly Gly Ala Thr Lys Thr
65                  70                  75                  80

Glu Ile Lys Gln Ala Ile Lys Val Met Asp Pro Ile Glu Glu Glu Glu
                85                  90                  95

Ser Thr Glu Lys Lys Val Leu Pro Ser Ser Asp Gly Lys Thr Pro Ala
            100                 105                 110

Glu Lys Lys Leu Lys Pro Ser Thr Asn Thr Lys Lys Lys Val Ser Phe
        115                 120                 125

Thr Pro Asn Glu Pro Gly Lys Tyr Thr Lys Leu Glu Lys Asp Ala Leu
    130                 135                 140

Asp Leu Leu Ser Asp Asn Glu Glu Asp Ala Glu Ser Ser Ile Leu
145                 150                 155                 160

Thr Phe Glu Glu Arg Asp Thr Ser Ser Leu Ser Ile Glu Ala Arg Leu
                165                 170                 175

Glu Ser Ile Glu Glu Lys Leu Ser Met Ile Leu Gly Leu Leu Arg Thr
            180                 185                 190

Leu Asn Ile Ala Thr Ala Gly Pro Thr Ala Ala Arg Asp Gly Ile Arg
        195                 200                 205

Asp Ala Met Ile Gly Val Arg Glu Glu Leu Ile Ala Asp Ile Ile Lys
    210                 215                 220

Glu Ala Lys Gly Lys Ala Ala Glu Met Met Glu Glu Met Ser Gln
225                 230                 235                 240

Arg Ser Lys Ile Gly Asn Gly Ser Val Lys Leu Thr Glu Lys Ala Lys
                245                 250                 255
```

```
Glu Leu Asn Lys Ile Val Glu Asp Ser Thr Ser Gly Glu Ser Glu
            260                 265                 270

Glu Glu Glu Pro Lys Asp Thr Gln Asp Asn Ser Gln Glu Asp Asp
        275                 280                 285

Ile Tyr Gln Leu Ile Met
    290

<210> SEQ ID NO 26
<211> LENGTH: 394
<212> TYPE: PRT
<213> ORGANISM: Human metapneumovirus
<220> FEATURE:
<221> NAME/KEY: MISC_FEATURE
<222> LOCATION: (1)..(394)
<223> OTHER INFORMATION: nucleocapsid protein N (Swissprot Q91F57)

<400> SEQUENCE: 26

Met Ser Leu Gln Gly Ile His Leu Ser Asp Leu Ser Tyr Lys His Ala
1               5                   10                  15

Ile Leu Lys Glu Ser Gln Tyr Thr Ile Lys Arg Asp Val Gly Thr Thr
            20                  25                  30

Thr Ala Val Thr Pro Ser Ser Leu Gln Gln Glu Ile Thr Leu Leu Cys
        35                  40                  45

Gly Glu Ile Leu Tyr Ala Lys His Ala Asp Tyr Lys Tyr Ala Ala Glu
    50                  55                  60

Ile Gly Ile Gln Tyr Ile Ser Thr Ala Leu Gly Ser Glu Arg Val Gln
65                  70                  75                  80

Gln Ile Leu Arg Asn Ser Gly Ser Glu Val Gln Val Val Leu Thr Arg
                85                  90                  95

Thr Tyr Ser Leu Gly Lys Ile Lys Asn Asn Lys Gly Glu Asp Leu Gln
            100                 105                 110

Met Leu Asp Ile His Gly Val Glu Lys Ser Trp Val Glu Glu Ile Asp
        115                 120                 125

Lys Glu Ala Arg Lys Thr Met Ala Thr Leu Leu Lys Glu Ser Ser Gly
    130                 135                 140

Asn Ile Pro Gln Asn Gln Arg Pro Ser Ala Pro Asp Thr Pro Ile Ile
145                 150                 155                 160

Leu Leu Cys Val Gly Ala Leu Ile Phe Thr Lys Leu Ala Ser Thr Ile
                165                 170                 175

Glu Val Gly Leu Glu Thr Thr Val Arg Arg Ala Asn Arg Val Leu Ser
            180                 185                 190

Asp Ala Leu Lys Arg Tyr Pro Arg Met Asp Ile Pro Lys Ile Ala Arg
        195                 200                 205

Ser Phe Tyr Asp Leu Phe Glu Gln Lys Val Tyr His Arg Ser Leu Phe
    210                 215                 220

Ile Glu Tyr Gly Lys Ala Leu Gly Ser Ser Thr Gly Ser Lys Ala
225                 230                 235                 240

Glu Ser Leu Phe Val Asn Ile Phe Met Gln Ala Tyr Gly Ala Gly Gln
                245                 250                 255

Thr Met Leu Arg Trp Gly Val Ile Ala Arg Ser Ser Asn Asn Ile Met
            260                 265                 270

Leu Gly His Val Ser Val Gln Ala Glu Leu Lys Gln Val Thr Glu Val
        275                 280                 285

Tyr Asp Leu Val Arg Glu Met Gly Pro Glu Ser Gly Leu Leu His Leu
    290                 295                 300

Arg Gln Ser Pro Lys Ala Gly Leu Leu Ser Leu Ala Asn Cys Pro Asn
305                 310                 315                 320
```

```
Phe Ala Ser Val Val Leu Gly Asn Ala Ser Gly Leu Gly Ile Ile Gly
            325                 330                 335

Met Tyr Arg Gly Arg Val Pro Asn Thr Glu Leu Phe Ser Ala Ala Glu
            340                 345                 350

Ser Tyr Ala Lys Ser Leu Lys Glu Ser Asn Lys Ile Asn Phe Ser Ser
            355                 360                 365

Leu Gly Leu Thr Asp Glu Glu Lys Glu Ala Ala Glu His Phe Leu Asn
            370                 375                 380

Val Ser Asp Asp Ser Gln Asn Asp Tyr Glu
385                 390
```

PREPARATION OF SOLUBLE N-PROTEIN/TRUNCATED P-PROTEIN COMPLEXES OF THE PARAMYXOVIRIDAE FAMILY

The invention relates to a method for the preparation of a N protein/truncated P protein soluble complex of a virus of the Paramyxoviridae family, to the complexes thus prepared, and also to the soluble N proteins which may be isolated from these complexes. The invention also relates to vaccine compositions comprising these N protein/truncated P protein complexes or Paramyxoviridae N proteins. Preferably, the truncated P protein is a C-terminal fragment of the P protein.

In France, as in most countries, bovine respiratory syncytial virus (RSV) is the main agent responsible for severe respiratory diseases in calves (bronchiolitis, pneumonia) in more than 70% of farms and in approximately 70% of calves during the first year of life (Perrin et al., 1979; Ames, 1993; Elvander, 1996). The death rate can be as high as 20% (Wellemans, 1992). It is a real scourge for stockbreeders who witness each year in winter powerlessly the systematic onset of this disease. There is therefore a strong demand among stockbreeders in this regard for the development of an effective prophylaxis. Vaccines are commercially available but in reality they are hardly effective or ineffective.

The same disease is found in humans: it is the agent responsible for neonatal bronchiolitis (see the journal Virologie No. 7, special edition, October 2003: respiratory syncytial virus infections in paediatrics). The data concerning the human disease is more precise. In France, in humans as in bovines, it is a disease which is epidemic in winter. 70% of infants are infected by RSV during the first year of life and 100% during the first two years. 500,000 children are therefore affected each year in France. A disease of the lower respiratory tract (bronchiolitis) occurs in 20% of infants affected and the hospital admission rate varies from 2 to 5% in France, for a period of 8 to 9 days, from 10 to 25% in premature babies, 14 to 45% in the case of pulmonary dysplasia, 15 to 25% in the case of a congenital heart defect. Approximately 10% of patients admitted to hospital have to be treated in an intensive care unit. The death rate is about 0.1%. A recent report by the World Health Organization estimated that 64 million people across the world are infected each year and that 160,000 deaths may be caused by RSV. Each year in the United States, from 18,000 to 75,000 people are admitted to hospital and almost 2,000 deaths are caused directly and 17,000 indirectly by the virus (Magon and Barik, 2004). RSV is also believed to be responsible for one third of flu symptoms in adults. In fact, it has been estimated that RSV kills four times as many elderly people as it does children. All told, RSV is said to claim from 3 to 5 million lives each year. Moreover, there is some evidence that this disease increases the risk of developing asthma during adulthood when it is contracted at a very young age (up to 4 months) by complex immunological mechanisms of which our understanding is still far from complete.

Although human and bovine RSV are two separate viruses, they are very closely related structurally, molecularly, antigenically, in terms of the disease which they cause (clinical picture, seasonality of the infections, infection of the young) and in terms of the fact that there are neither an effective vaccine nor antiviral agents apart from a monoclonal antibody which is extremely expensive and therefore rarely used and an ineffective and fairly toxic antiviral agent which in fact deprives the cells of ATP.

In the 1960s, vaccination tests were carried out in the United States on young children with formalin-fixed virus. The results were disastrous: the vaccinated children developed exacerbated symptoms during natural infection by the virus some months later and several of them even died.

Following these unsuccessful tests, there is still no vaccine against this disease for humans and the efficacy of the vaccines sold for bovines is highly doubtful, although no serious study of the subject has been carried out in France. However, a plurality of vaccines have been withdrawn from the market after post-vaccine accidents in bovines.

It is difficult to develop a vaccine against RSV for the following reasons:

(1) natural infection does not impart protective immunity against reinfection, as the local immune memory against RSV has a short duration;

(2) the induction of strong cellular and humoral immunity is associated with an increase in the severity of the disease (sensitisation by vaccination);

(3) there is no adjuvant or vaccine strategy allowing effective mucosal vaccination;

(4) newborn children (aged less than two months) are the main target of the vaccination; however, their immune system responds badly to conventional vaccines;

(5) the presence of maternal antibodies in the blood does not prevent infection;

(6) variability is observed in the virus strains in circulation.

Subunit vaccines are currently being developed, some based on the G surface protein. New types of vaccines obtained by reverse genetics (i.e. by strain attenuation by genetic modification) have been being developed for a number of years, both for HRSV and for BRSV. To date, no use of an attenuated strain has been approved for human beings. This is probably due to the fact that attenuated strains trigger a weak immune response.

DNA vaccines based on the F and G membrane proteins of HRSV or BRSV are currently being developed, partly in calves (Taylor et al. 2005, Martinez et al. 1999). This type of vaccine imparts protective immunity which some studies have found to be associated with immunopathology. The efficacy of these vaccines needs to be improved.

RSV is an enveloped virus having a single-stranded RNA negative genome. This RNA encodes 11 proteins and is packaged by the nucleocapsid (N) protein and associated with the polymerase complex composed of two proteins, the L (large) protein or polymerase and the P cofactor (phosphoprotein) (FIG. 1). This molecule has a crucial role in the function of the polymerase: P enables L to recognize genomic RNA. There are also two cofactors for RSV, M2-1 and M2-2, which have a role of processivity (M2-1) and of regulating the transcription/replication balance (M2-2).

On the surface of the virus particle there are two major proteins, F and G. The F protein enables fusion of the viral envelope with cell membranes and is involved in the formation of syncytia. The G protein enables attachment of the virus to the cell surface. The M (matrix) protein acts as an intermediary between the viral envelope and the polymerase/genome complex. The two surface proteins, F and G, are the RSV major immunogenic proteins, as they are the targets of neutralising antibodies.

However, studies carried out on mice have shown that the G protein is involved in the induction of Th2-type immunopathological vaccine responses (IL-4 and IL-5 production and recruitment of eosinophils) (Sparer et al. 1998). In bovines, on the other hand, neither of these two proteins has been associated with immunopathological responses and both allow the establishment of protective responses (Taylor et al. 1997).

Current research into new vaccine candidates focuses mainly on F and G proteins.

However, in humans and bovines, cell-mediated immunity and, in particular, the cytotoxic T response is a crucial component of the protection against RSV. In humans as in bovines, the N protein is the main support of the cytotoxic T responses (Goulder et al., 2000). Calves are a relevant model for vaccination against RSV. It has been found that the use of recombinant vaccine expressing the RSV N protein generated a cellular-type (Th1) response allowing the immune response to be rebalanced (Taylor et al. 1997; Gaddum et al., 2003). All of the current studies therefore argue in favour of an anti-RSV vaccine formed by the association of a plurality of proteins, in particular F and G surface proteins and the N internal protein.

The N protein is the protein which is the most expressed in the infected cell and one of the most numerous proteins in the virus particles (Collins et al., 2001). It surrounds the viral genome consisting of a single-stranded RNA, forming large helical structures. When it is expressed alone in recombinant form, the N protein polymerises non-specifically on the cellular RNAs. It then forms very large, insoluble and non-purifiable (RNA/N) helical structures which resemble the nucleocapsids observed in infected cells (Méric et al., 1994; Bhella et al., 2002).

This N protein is capable of interacting with the RSV P protein, the viral L-polymerase cofactor. Mapping studies of the interaction domains using basically the double hybrid system and coimmunoprecipitation have been carried out by various teams, the screen being negative (loss of interaction). The C-terminal domain of the human or bovine virus P protein was suspected of having an important role in the interaction with the N protein (Garcia Barreno et al., 1996; Mallipeddi et al., 1996; Slack and Easton, 1998; Khattar et al., 2001a, 2001b). However, it was argued that the double hybrid system did not reflect the real nature of the interactions between the N and P proteins (Khattar et al., 2001a). Furthermore, the exact nature of the P-N complexes (number of each molecule or stoichiometry, structure) was not described and the interaction domains neither demonstrated nor characterised.

Studies carried out on closely related viruses belonging to the Paramyxoviridae family (Sendai virus, measles, or measles virus) gave rise to the idea that the P protein would form a soluble complex with the N protein, denoted by N°P, preventing it from fixing non-specifically to cellular RNAs (Kolakofsky et al., 2004). The P protein was also believed to be capable of recognizing the nucleocapsid composed of the N protein packaged RNA, since P acts as the cofactor of L, enabling it to "find" its substrate.

For the Paramyxoviridae, two interaction domains have been found in P. The first, located in the C-terminal position of the protein, is said to form the domain recognising the N-RNA complex, the one located in the N-terminal position enabling the formation of N°P complexes (Kolakowsky et al., 2004). For RSV, these complexes have not been clearly identified and the role of the C-terminal domain of the P protein interacting with N has not been clearly defined.

To date, the development of a subunit vaccine based on the N protein has been impossible because of the difficulty of isolating the N protein in soluble form.

Recently, the inventors have developed a bacterial P and N proteins coexpression system by selecting RSV as the Paramyxoviridae model (Castagné et al., 2004). The P protein has been fused to glutathione-S-transferase (GST) in an ampicillin resistant plasmid; the N protein has been cloned in a kanamycin resistant plasmid. Coexpression of these plasmids in the same bacteria has enabled the GST-P fusion protein to be purified and the N protein to be carried with the fusion protein.

However, no doubt owing to lingering solubility problems, the rates of production of N protein in soluble form remain largely insufficient to allow implementation of the system on an industrial scale. Furthermore, the nature of the N protein thus produced has not been characterised.

The inventors have demonstrated that the coexpression of N-terminal deletion mutants of the protein with the N protein of RSV allows the purification of large amounts of N protein much greater than those obtained with the entire P protein.

DEFINITIONS

The "Paramyxoviridae" family encompasses the Paramyxovirinae and Pneumovirinae sub-families. The Paramyxovirinae include the Respiroviruses, the prototype virus of which is Sendai virus, and the Rubulaviruses (in particular the mumps virus) and the Morbilliviruses such as measles virus. Each of the Respirovirus and Rubulavirus genera encompasses strains of the parainfluenza virus. The Pneumovirinae sub-family encompasses two genera, the *Pneumoviruses* and the *Metapneumoviruses*, the latter genus including human *Metapneumovirus*. Human respiratory syncytial virus (RSV) is the prototype virus of the Pneumovirus genus belonging to the Pneumovirinae sub-family. The *Pneumoviruses* also include bovine and murine strains of RSV.

Unless otherwise specified, the term "respiratory syncytial virus" refers generally to RSV, whatever the form (human, bovine, etc), the subgroup (for example, the A, B and S subgroups identified in human RSV) or the strain in question.

The term "protein" denotes the Phosphoprotein or P protein forming part of the Polymerase complex of a virus of the Paramyxoviridae family. The P protein is a cofactor of the viral (replicase/transcriptase) polymerase and can be phosphorylated. The Paramyxoviridae P proteins sequences are known to a person skilled in the art. For example, the P protein of the Long strain of human RSV has a sequence of 241 amino acids that has been deposited in the Swissprot database under accession number P12579. This sequence is shown in the sequence SEQ ID No. 1. The bovine RSV P protein also comprises 241 amino acids (SEQ ID No. 23). Sendai virus (Harris strain), measles virus (Edmonston B strain), mumps virus (SBL-1 strain) and human *Metapneumovirus* (00-1 strain) proteins P are also described in the Swissprot database under accession numbers P04859 (SEQ ID No. 2), CAA91364 (SEQ ID No. 3), P19717 (SEQ ID No. 4) and Q91KZ5 (SEQ ID No. 5) respectively. The term "protein" can denote an entire P protein, a truncated P protein or a fragment of the P protein.

The Paramyxoviridae P protein forms homo-oligomers, in particular homotetramers, for example in the Sendai virus or RSV. For RSV, a domain of the P protein capable of oligomerising (P-P oligomerisation) has been mapped in amino acids 120 to 150 of this protein (Castagné et al., 2004). Thus, for example, the fragment consisting of amino acids 161 to 241 of the RSV P protein does not form oligomers. The oligomerisation domain of the Sendai virus P protein has been described by Tarbouriech et al. (2000) as consisting of residues 320 to 446 of the P protein. Moreover, the P oligomerisation region has been identified at amino acids positions 304-376 for the measles virus P protein (Johansson et al., 2003).

The term "truncated protein" denotes a P protein in which one or more sequences of contiguous amino acids have been suppressed. This may be the truncation of a C-terminal sequence, an N-terminal sequence, an "internal" sequence relative to the P protein primary sequence, or a combination of these truncations.

The truncated P proteins according to the invention are devoid of the P oligomerisation domain and are capable of interacting with the N protein. As the interaction domain of the Paramyxoviridae P protein with the N protein has been mapped at the C-terminal end, examples of truncated P protein preferably include a C-terminal fragment of the P protein, or a "chimeric" P protein formed by the fusion of a C-terminal fragment of the P protein (capable of interacting with the N protein) with at least one other sequence of contiguous amino acids of the P protein. Said C-terminal fragment and said other sequence of the P protein are not themselves naturally contiguous and do not have sequence overlap. For example, a truncated RSV P protein can have the sequence consisting of amino acids 1 to 121 and 161 to 241 of the native P protein. A "fragment" of a reference polypeptide denotes any sequence of contiguous amino acids found in the sequence of the reference polypeptide.

The term "P protein fragment" or "PΔ" denotes a polypeptide, the sequence of which comprises a chain of amino acids of the P protein, one or more consecutive amino acids of the P protein having been suppressed from the N-terminal and/or C-terminal end.

The term "C-terminal fragment of the protein" or "PΔN" denotes a P protein in which one or more consecutive amino acids have been suppressed from the N-terminal end. Preferably, a C-terminal fragment of the P protein denotes a chain of amino acids positioned in the C-terminal half of the primary sequence of the P protein (if the sequence contains an odd number of amino acids, an additional amino acid can be allocated arbitrarily to the C-terminal half of the protein relative to the N-terminal half). For example, for the RSV P protein that comprises 241 amino acids, PΔ161N denotes a C-terminal fragment consisting of amino acids 161 to 241 of the P protein. Likewise for example, for the measles virus (Edmonston B strain) P protein that comprises 507 amino acids, PΔ386N denotes a C-terminal fragment consisting of amino acids 386 to 507 of the P protein.

The term "N-terminal fragment of the protein" or "PΔC" refers to a P protein in which one or more consecutive amino acids have been suppressed from the C-terminal end.

The term "internal fragment of the protein" or "PΔNC" refers to a P protein in which one or more consecutive amino acids have been suppressed from the N-terminal end and one or more consecutive amino acids have been suppressed from the C-terminal end.

The term "N protein" denotes the Paramyxoviridae nucleocapsid protein that forms helical structures to surround the viral genome. The human RSV Long strain N protein has a sequence of 391 amino acids that is described in sequence SEQ ID No. 6. The bovine RSV N protein also comprises 391 amino acids (see SEQ ID No. 24). Sendai virus (Hamamatsu strain), measles virus (Edmonston B strain), mumps virus (SBL-1 strain) and human *Metapneumovirus* (00-1) N proteins are also described in the Swissprot database under accession numbers Q9DUE3 (SEQ ID No. 7), Q89933 (SEQ ID No. 8), P21277 (SEQ ID No. 9) and Q91F57 (SEQ ID No. 10) respectively.

The P and N proteins sequences described hereinbefore have an illustrative character, these sequences being likely to display variations according to the particular strain considered for a given virus. Thus, the amino acid positions mentioned in the present application are stated relative to these reference sequences. A person skilled in the art will be quite capable of identifying the corresponding domains in virus strains other than those exemplified.

The coding sequences of these N and P proteins of a virus of the Paramyxoviridae family are also known to a person skilled in the art.

The term "tag protein" denotes a protein which is used in fusion with a relevant protein to facilitate purification thereof. Tag proteins are known to a person skilled in the art. Examples of tag proteins include glutathione-S-transferase (GST) or histidine tags which are sequences generally comprising a chain of 4 to 10 histidine residues.

In the context of the invention, the term "homologous" relates to the relationship existing between proteins having a single evolutionary origin, for example homologous proteins belonging to various species or, in the case of viruses, virus strains. Proteins of this type (and the encoding genes thereof) have sequence homologies, reflected by the similarity of their sequences, either in terms of the percentage of similarity or in terms of the presence of specific residues or motifs in conserved positions.

The term "sequences similarity" denotes the degree of identity between nucleic acid or amino acid sequences of proteins that may or may not share a single evolutionary origin. As is conventional, the terms "homology" and "similarity" are used interchangeably. Two amino acid sequences are said to be "essentially homologous" if their amino acids are at least 80% identical or at least 90% similar (i.e. functionally identical). Similar or homologous sequences can be identified by alignment, using for example the BLAST or FASTA programs.

The solubility of the proteins or complexes according to the invention is defined relative to a buffered aqueous medium such as 1×PBS; a 10 mM Tris buffer (pH 7.4-8.0), 150 mM NaCl; 0.2×TBE, or else for example a bacteria lysis buffer comprising 50 mM Tris-HCl (pH 7.8), 60 mM NaCl, 1 mM EDTA, 2 mM DTT, 0.2% Triton X-100, 10 mM MgSO$_4$, 1 mM CaCl$_2$ and 1 mg/ml lysozyme.

Method for the Preparation of a N Protein/Truncated P Protein Soluble Complex

The inventors have previously shown (Castagné et al., 2004) that the coexpression of plasmids encoding respectively a fusion of the P protein with GST and the N protein of a Paramyxoviridae allowed the GST-P fusion protein to be collected while carrying the N protein. The production rates of N-P complexes are, however, low to the point of not being compatible with industrial-scale production of these complexes.

The inventors have characterised P protein deletion mutants by determining their capacity to interact with the N protein. They have thus demonstrated that some of these mutants are capable not only of interacting with the N protein as an N-RNA complex or ribonucleocapsid (RNP) but also of allowing the preparation of N-P complexes at preparation rates much higher than those obtained with the entire P protein. These particular mutants correspond to P protein fragments that comprise the C-terminal portion of the molecule and are devoid of the P oligomerisation domain.

Coexpression of these P protein mutants with the N protein therefore allows the N protein to be prepared in large amounts as soluble RNP, in particular as N protein/truncated P protein complexes, in particular C-terminal fragment of P.

The invention therefore relates to a process or method for the preparation of a N protein/truncated P protein soluble complex of a virus of the Paramyxoviridae family, said process including the steps consisting in:

a) coexpressing an N protein of a virus of the Paramyxoviridae family with a truncated P protein of the same virus of the Paramyxoviridae family, said truncated P protein being devoid of the P oligomerisation domain and being capable to interact with the N protein;
b) collecting the so formed N protein/truncated P protein soluble complexes.

The truncated P protein preferably comprises a P protein C-terminal fragment. The interaction domain of the Paramyxoviridae P protein with the N protein, optionally an N—RNA complex form, is indeed located on the C-terminal side of the P protein.

The truncated P protein may be a "chimeric" P protein formed by the fusion of a C-terminal fragment of the P protein with at least one other sequence of contiguous amino acids of the P protein, as defined hereinbefore.

Preferably, the truncated P protein is a P protein C-terminal fragment.

The invention then relates to a process for the preparation of a N protein/C-terminal fragment of the P protein soluble complex ("N-PΔN complex") of a virus of the Paramyxoviridae family, said process including the steps consisting in:

a) coexpressing an N protein of a virus of the Paramyxoviridae family with a C-terminal fragment of the P protein of the same virus of the Paramyxoviridae family, said C-terminal fragment of the P protein being devoid of the P oligomerisation domain and being capable of interacting with the N protein;
b) collecting the so formed soluble N-PΔN complexes.

Said virus of the Paramyxoviridae family may be a Paramyxovirinae or a Pneumovirinae. In particular, the virus may be selected from the group consisting of the mumps virus, the measles virus, human *Metapneumovirus* and the parainfluenza virus. Preferably, the virus is a *Pneumovirus* such as human or bovine respiratory syncytial virus (RSV).

A person skilled in the art is familiar with or is capable of determining truncated P proteins, or more specifically C-terminal fragments of the P protein, that are capable of interacting with the N protein.

For example, in the case of RSV, the inventors have used the previously described (Castagné et al., 2004) strategy of coexpression of the N and P proteins in *E. Coli* to map the interaction domain between P and N. For this purpose, the N protein was coexpressed with GST fused P deletion mutants. The inventors have thus demonstrated that the interaction domain of P with N is located at the C-terminal end of the P protein (FIG. 1). More specifically, the inventors have showed that C-terminal fragments of P, up to an oligopeptide comprising the 9 C-terminal amino acids of the RSV P protein (amino acids 233 to 241), are capable of interacting with the N protein.

Moreover, it has been described, for example, that the interaction domain of the Sendai virus P protein with the N protein in the form of an N-RNA complex or RNP, known as the "X-domain" or XD, is defined by amino acids 473 to 568 (Kolakofsky et al. 2004).

For the other Paramyxoviridae, if appropriate, a person skilled in the art is capable of identifying in the P protein the domain interacting with the N protein in the form of a nucleocapsid using the strategy described by the inventors.

The inventors have also demonstrated that specific C-terminal fragments of the RSV P protein, namely the PΔ161N fragment (amino acids 161 to 241), allowed the preparation of large amounts of N protein compared to the entire P protein which, in practice, does not allow sufficient yields on an industrial scale. The smallest deletion mutants, down to PΔ233N (amino acids 233 to 241) which contain only 9 amino acids, enable to obtain yields comparable to those of PΔ161N.

These fragments which are smaller than PΔ161N correspond to fragments of the RSV protein that are capable of interacting with the N protein and that are no longer capable of oligomerising and therefore are devoid of the P oligomerisation domain. That is to say, the RSV minimum P oligomerisation domain would be defined by roughly amino acids 120 to 150 of the P protein.

This same strategy has enabled the inventors to show that a C-terminal fragment of the measles virus P protein, consisting of amino acid residues 386-507 (PΔ386N), interacted with the N protein of this virus and allowed purification thereof. Conversely, deletion of the N-terminal portion of the P protein, up to residue 456 (inclusive; PΔ457N fragment), does not allow the N protein to be purified. The structure of the C-terminal region of the P protein interacting with the ribonucleocapsid has been determined by Johansson et al. (2003). The P oligomerisation region has been determined, by deletions and prediction, as being defined by amino acids 304-376.

The use of C-terminal fragments of the P protein that contain the interaction domain with the N protein in a RNP form but in which the P oligomerisation domain has been deleted therefore enables both interaction of the P fragments with N and the formation of N-PΔN soluble complexes and also the production of these complexes at a high yield. It is assumed, without thereby being linked to any one particular mechanism, that the absence of the P oligomerisation domain eliminates problems of insolubility of the N-ΔPN complexes linked to interactions between P proteins of these complexes.

Thus, according to one embodiment, the process for the preparation of an N-PΔN complex involves the expression of a C-terminal fragment of the RSV P protein that comprises the last 9 C-terminal amino acids of the RSV P protein and that is devoid of at least the 119, preferably the 149, more preferably the 160 N-terminal amino acids of the RSV P protein.

More specifically, in the process according to the invention, there can be coexpressed with the RSV N protein:

a) a C-terminal fragment of the RSV P protein that comprises the sequence of amino acids 233 to 241 of the human RSV LONG strain P protein as shown in SEQ ID No. 1 and that extends in the N-terminal direction up to an amino acid residue between positions 233 and 120, preferably 150, more preferably 161 of the sequence of the RSV P protein as shown in SEQ ID No. 1, or
b) a C-terminal fragment, homologous to the fragment defined in a), of a P protein from another human RSV strain or from a bovine RSV strain.

The C-terminal fragment of the RSV P protein may, for example, be selected from the group consisting of PΔ120N (amino acids 120 to 241 of P), PΔ150N (amino acids 150 to 241 of P), PΔ161N (amino acids 161 to 241 of P), PΔ180N (amino acids 180 to 241 of P), PΔ200N (amino acids 200 to 241 of P), PΔ220N (amino acids 220 to 241 of P), PΔ230N (amino acids 230 to 241 of P) and PΔ233N (amino acids 233 to 241 of P).

The invention also relates to a process wherein the RSV N protein is coexpressed with a truncated P protein comprising a C-terminal fragment of the RSV P protein as described hereinbefore that comprises the last 9 C-terminal amino acids of the RSV P protein and that is devoid of at least the 119, preferably the 149, more preferably the 160 N-terminal amino acids of the RSV P protein.

For example, the truncated P protein comprising a C-terminal fragment of the P protein can be formed by the fusion of the last 122 N-terminal amino acids with the last 80 C-terminal amino acids of the RSV P protein; it can, for example, be formed by the sequence of amino acids 1 to 121 and 161 to 241 of the P protein of the human RSV LONG strain as shown in SEQ ID No. 1.

According to a further embodiment, the Paramyxoviridae is the measles virus and the process for the preparation of an N-PΔN complex involves the expression of a C-terminal fragment of the measles virus P protein comprising at most, or consisting of, the 122 C-terminal amino acids of the P protein. The fragment may, in particular, be a C-terminal fragment consisting of amino acids 386 to 507 of the P protein (PΔ386N) of the measles virus Edmonston B strain, as shown in SEQ ID No. 3, or a C-terminal fragment, homologous to that defined for the Edmonston strain P protein, of a P protein from another measles virus strain.

Any desired conventional technology of molecular biology, microbiology or recombinant DNA can be employed to carry out the process according to the invention. Such technologies are within the grasp of a person skilled in the art and have been described, namely, in Sambrook, Fritsch & Maniatis, Molecular Cloning: A Laboratory Manual, Second Edition (1989) Cold Spring Harbor Laboratory Press, Cold Spring Harbor, N.Y. ("Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription and Translation [B. D. Hames & S. J. Higgins, eds. (1984)]; Animal Cell Culture [R. I. Freshney, ed. (1986)]; Immobilized Cells and Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

The term "to express" or "expression" means allowing or ensuring the information contained in a gene or a DNA sequence to become manifest, for example by producing a protein by activation of the cell functions involved in the transcription and the translation of the corresponding genetic or DNA sequence. The term "coexpression" is used when the information contained in two genes or DNA sequences is expressed in a single host cell.

A "coding sequence" denotes a nucleotide sequence which, when expressed, results in the production of RNA, a polypeptide, a protein, etc. A protein-coding sequence generally contains a start codon (ATG) and a stop codon.

A coding sequence is "under the control of" or "functionally associated with" transcriptional and translational control sequences when a RNA polymerase transcribes the coding sequence into RNA, in particular into mRNA, which may then be spliced if it contains introns, and translated into the protein coded by the coding sequence.

The terms "vector", "cloning vector" and "expression vector" denote the vehicle by which a DNA or RNA sequence (for example, a heterologous gene) can be introduced into a host cell so as to transform the host cell and to promote the expression of the introduced sequence. Examples of vectors include plasmids, phages, viruses. The most common vectors are plasmids which are autonomous replication units, generally of bacterial origin, and which may be double-stranded DNA. Plasmids can easily integrate an exogenous DNA sequence which can then easily be introduced into an appropriate host. A plasmid vector generally contains a coding DNA sequence, a promoter DNA sequence and has one or more restriction sites allowing an exogenous DNA to be introduced. Non-limiting examples of plasmids include the pKK (Clonetech), pUC and pET (Novagen, Inc., Madison, Wis.), pRSET or pREP (Invitrogen, San Diego, Calif.), pMAL (New England Biolabs, Beverly, Mass.), or pGEX-4T-3 (Pharmacia) plasmids.

The term "host cell" refers to any cell or organism which is selected, modified, cultivated or manipulated for the production of a substance by the cell, for example the expression by the cell of a gene, a DNA or RNA sequence, a protein or an enzyme.

An "expression system" denotes a host cell and a compatible vector used under appropriate conditions to produce a protein encoded by an exogenous DNA carried by the vector and introduced into the host cell. Conventional expression systems include *E. coli* host cells and plasmid vectors, insect cells and Baculovirus vectors or mammalian cells and vectors.

The expression system according to the process of the invention is advantageously a bacterial expression system, in particular in *E. coli*, with, for example, pGEX-4T-3 as the vector. This is because bacterial systems are the expression systems which generally provide the highest production rates.

Advantageously, the truncated P protein, and in particular the C-terminal fragment of the P protein, is expressed as a fusion with a protein facilitating purification of the N protein/ truncated P protein complexes, in particular a protein which can be used in affinity chromatography. It may be a tag protein such as glutathione-S-transferase (GST), in which case the truncated P protein/GST fusion protein can be isolated by chromatography on a solid support coupled to glutathione. Other tags can be used as the polyhistidine or "his-tag".

There are thus obtained N protein/truncated P protein-tag protein complexes (GST or another tag protein fused with the truncated P protein, in particular the PΔN fragment) in which the tag protein can be removed by enzymatic cleavage. For example, GST can be removed by thrombin cleavage or by any other appropriate enzyme if the fusion comprises a protein other than GST.

Specific examples of the construction of vectors allowing the process according to the invention to be carried out are described in the following examples.

N Protein/Truncated P Protein Soluble Complexes

The process for the preparation of a N protein/truncated P protein, in particular a C-terminal fragment of the P protein, soluble complex as described hereinbefore allows N protein/ truncated P protein complexes to be easily obtained in isolated or purified form.

The invention therefore also relates to a N protein/truncated P protein soluble complex of a virus of the Paramyxoviridae family obtainable by a preparation process according to the invention.

Preferably, the truncated P protein comprises or is a C-terminal fragment of the P protein.

The invention relates more specifically to a N protein/C-terminal fragment of the P protein soluble complex ("N-PΔN complex") of a virus of the Paramyxoviridae family obtainable by a preparation process according to the invention.

Said virus of the Paramyxoviridae family may be a Paramyxovirinae or a Pneumovirinae. In particular, the virus may be selected from the group consisting of the mumps virus, the measles virus, human *Metapneumovirus* (HMPV) and parainfluenza virus. Preferably, the virus is a *Pneumovirus* such as the respiratory syncytial virus (RSV) for example the human or bovine RSV.

According to one embodiment, the Paramyxoviridae virus is the respiratory syncytial virus (RSV) and said C-terminal fragment of the P protein comprises the last 9 C-terminal amino acids of the RSV P protein and is devoid of at least the 119, preferably the 149, more preferably the 160 N-terminal amino acids of the RSV P protein.

More specifically, said C-terminal fragment of the P protein may comprise a) the sequence of amino acids 233 to 241 of the P protein of the LONG strain of human RSV as shown in SEQ ID No. 1 and extend in the N-terminal direction up to an amino acid residue between positions 233 and 120, preferably 150, more preferably 161 of the sequence of the RSV P protein as shown in SEQ ID No. 1, or b) a C-terminal fragment, homologous to the fragment defined in a), of a P protein from another human RSV strain or from a bovine RSV strain.

The fragment may, in particular, be a C-terminal fragment of the P protein selected from the group consisting of PΔ120N, PΔ150N, PΔ161N, PΔ180N, PΔ200N, PΔ220N, PΔ230N and PΔ233N.

The invention also relates to a soluble complex containing a truncated RSV P protein comprising a C-terminal fragment of the RSV P protein as described hereinbefore that comprises the last 9 C-terminal amino acids of the RSV P protein and that is devoid of at least the 119, preferably the 149, more preferably the 160 N-terminal amino acids of the RSV P protein.

For example, the truncated RSV P protein comprising a C-terminal fragment of the P protein can be formed by the fusion of the last 122 N-terminal amino acids with the last 80 C-terminal amino acids of the RSV P protein; it may, for example, be formed by the sequence of amino acids 1 to 121 and 161 to 241 of the P protein of the human RSV LONG strain as shown in SEQ ID No. 1.

According to a further embodiment, the Paramyxoviridae virus is measles virus and said fragment of the P protein is a C-terminal fragment of the P protein that comprises at most, or consists of, the 122 C-terminal amino acids of the P protein. More specifically, said C-terminal fragment of the measles virus P protein can consist of acids 386 to 514 of the P protein (PΔ386N) of the Edmonston B strain of measles virus, as shown in SEQ ID NO. 3, or be a C-terminal fragment, homologous to the one defined for the Edmonston strain P protein, of a P protein from another measles virus strain.

In the N-PΔN complex, the PΔN protein may optionally be present as a fusion with a tag protein, for example GST, a histidine tag or any other appropriate protein facilitating the N-PΔN complexes purification.

The electron microscope analysis of the complexes produced for RSV revealed that they were composed of rings containing 10 N protein molecules, these soluble rings also containing a small RNA of approximately 70 bases, which was visible by agarose gel electrophoresis (FIG. 3). These complexes contain a similar amount of N proteins and PΔN-GST proteins. The RNA cannot be dissociated from the N protein ring without denaturation of this protein.

Thus, the invention also relates to an N protein/C-terminal fragment respiratory syncytial virus (RSV) of the P protein isolated soluble complex, comprising 10 molecules of N protein, each or the majority of which being associated with a C-terminal fragment of the P protein, wherein said C-terminal fragment of P comprises the last 9 C-terminal amino acids of the RSV P protein and is devoid of at least the 160 N-terminal amino acids of the RSV P protein, as defined hereinbefore. This RSV N-PΔN complex further comprises an RNA of approximately 70 bases.

Methods for the Preparation of Soluble N Protein

The soluble N protein can easily be isolated in the form of rings with their RNA, from these N protein/truncated P protein complexes, or more specifically N-PΔN, for example by size exclusion chromatography (gel filtration). This separation can be carried out, if appropriate, after separation, by enzymatic cleavage, of the truncated P protein and of the tag protein to which the truncated P protein is optionally fused.

The invention therefore also relates to a process for the preparation of soluble N proteins of a virus of the Paramyxoviridae family, said process including the steps consisting in:

a) preparing a N protein/truncated P protein soluble complex by a process as defined hereinbefore; and b) separating the N proteins from the soluble N protein/truncated P protein soluble complexes.

Preferably, the truncated P protein comprises or is a C-terminal fragment of the P protein.

The invention relates more specifically to a process for the preparation of soluble N proteins of a virus of the Paramyxoviridae family, said process including the steps consisting in:

a) preparing a N protein/C-terminal fragment of the P protein soluble complex ("N-PΔN complex") by a process as defined hereinbefore; and b) separating the soluble N proteins from the soluble N-PΔN complexes.

Said virus of the Paramyxoviridae family may be a Paramyxovirinae or a Pneumovirinae. In particular, the virus may be selected from the group consisting of mumps virus, measles virus, human *Metapneumovirus* and parainfluenza virus. Preferably, the virus is a *Pneumovirus* such as the, for example human or bovine, respiratory syncytial virus (RSV).

The soluble N proteins of a virus of the Paramyxoviridae family obtainable by the foregoing process are also part of the invention.

In the case of RSV, the N protein has an apparent mass of 450 kDa, whereas the largest usable C-terminal fragment of the P protein (PΔ161N) have a mass of 15 kDa. The N protein rings can therefore be separated from the P protein C-terminal fragments, for example by chromatography over a Sephadex column as described in the following Example 3 (and FIG. 2).

According to one embodiment, the invention therefore proposes soluble RSV N proteins, said N proteins being associated in rings having a diameter of about 7 nm and containing 10 subunits. However, it is also possible that some rings are partial and contain less than 10 subunits. The rings furthermore contain an RNA of approximately 70 bases.

Vaccine Compositions

The RSV N protein, and more generally of the Paramyxoviridae, is an interesting antigen for vaccination, although to date no one has managed to purify it in soluble form. The process according to the invention allows very pure and very homogeneous ring-structured N proteins to be obtained easily and in large amounts.

In order to evaluate the immunogenic properties of the N protein in rings, the inventors immunised mice with a Paramyxoviridae N-PΔN complex according to the invention. For use as a vaccine, the N and PΔN proteins can optionally be separated; however, this operation is not necessary, the presence of PΔN having no adverse effect.

More specifically, the inventors immunised mice with the RSV N-PΔ161N complex and used the RSV PΔ161N polypeptide as a control.

In view of the specificity of this virus for the respiratory tract, two routes of immunisation were compared: the subcutaneous route, which is a conventional route of parenteral vaccination, and the nasal route, which allows local immunity to be induced in the respiratory mucosa and associated lymphoid tissues.

As it is difficult to obtain an immune response to a soluble recombinant protein in the absence of a vaccination adjuvant, the inventors also used the *E. coli* detoxified lymphotoxin, LT(R192G) (provided by Dr J. D. Clements, USA), the mucosal adjuvant properties of which have been well described (McNeal et al. 2002, Freytag and Clements 2005).

The immune response parameters which were followed are (i) the production of serum and mucus antibodies (by bronchoalveolar lavages) and (ii) the cell response via the production of IFN-γ by memory T lymphocytes isolated from the spleen or the lung.

In the presence of the LT(R192G) adjuvant, the N protein (N-PΔ161N complex) induces a strong production of serum antibodies whatever the route of administration (nasal or subcutaneous) (FIG. 4A). This response is detectable after the first immunisation (J14) and is amplified after the booster dose (J28). The adjuvant also allows production of antibodies against PΔ161N to be induced after the booster dose.

In a noteworthy manner, nasal and subcutaneous administration of the N-PΔ161N complex without an adjuvant generates a strong production of serum antibodies from the first immunisation. Under the same conditions, PΔ161N does not induce any response. A comparable response profile is observed for the production of the mucus antibodies, total Ig (FIG. 4B).

On the other hand, only the N protein (N-PΔ161N complex) administered nasally in the presence of LT(R192G) allows the production of IgA in the respiratory mucosa (FIG. 4B).

The cell response was measured in terms of the capacity of leucocytes from the spleen or lung to produce IFN-γ in vitro in the presence of N-PΔ161N or PΔ161 alone. IFN-γ is a cytokine produced by the CD4 and CD8 T lymphocytes. Memory T lymphocytes CD4 and CD8 can be reactivated in vitro in the presence of the antigen to which they are specific. IFN-γ is produced by the Th1 lymphocytes and the cytotoxic T lymphocytes which are the major effectors of the anti-viral defenses.

The strongest responses are obtained after restimulation with the N-PΔ161N complex (FIG. 5). As for the antibodies, nasal or cutaneous administration of N-PΔ161N stimulates peripheral cellular immunity (spleen) specific to N. In a noteworthy manner, N administered nasally with adjuvant generates local cellular immunity (lung) (FIG. 5).

In conclusion, the ring-structured N-protein has been found to be highly immunogenic, partly for stimulating a local response (respiratory mucosa).

The invention therefore proposes a vaccine composition comprising soluble N proteins of a virus of the Paramyxoviridae family, said soluble N proteins being in a pharmaceutically acceptable carrier. These soluble N proteins are, in particular, obtainable by a process for the separation of soluble N proteins from N protein/truncated P protein soluble complexes, more specifically N-PΔN, as described above.

As explained hereinbefore, the soluble N proteins can be used in vaccination in the form of a complex with the P protein without adverse effect. Accordingly, a vaccine composition according to the invention can comprise a N protein/P protein soluble complex of a virus of the Paramyxoviridae family, in a pharmaceutically acceptable carrier.

As far as the issue of the rate of production of these complexes is concerned, the invention preferably relates to a vaccine composition comprising a N protein/truncated P protein soluble complex of a virus of the Paramyxoviridae family, in a pharmaceutically acceptable carrier, in which said truncated P protein is devoid of the P oligomerisation domain and is capable of interacting with the N protein.

Preferably, the truncated P protein comprises or is a C-terminal fragment of the P protein.

The invention thus relates more specifically to a N protein/C-terminal fragment of the P protein soluble complex of a virus of the Paramyxoviridae family, in a pharmaceutically acceptable carrier, in which said C-terminal fragment of the P protein is devoid of the P oligomerisation domain and is capable of interacting with the N protein.

Said virus of the Paramyxoviridae family may be a Paramyxovirinae or a Pneumovirinae. In particular, the virus may be selected from the group consisting of mumps virus, measles virus and parainfluenza virus. Preferably, the soluble N proteins of a virus of the Paramyxoviridae family are soluble N proteins of the, for example human or bovine, respiratory syncytial virus (RSV).

According to one embodiment, the Paramyxoviridae virus is the respiratory syncytial virus (RSV) and said C-terminal fragment of the P protein is a C-terminal fragment (PΔN) that comprises the last 9 C-terminal amino acids of the RSV P protein and that is devoid of at least the 119, preferably the 149, more preferably the 160 N-terminal amino acids of the RSV P protein.

More specifically, in said composition, the C-terminal fragment of the RSV P protein may be:

a) a C-terminal fragment that comprises the sequence of amino acids 233 to 241 of the P protein of the human RSV LONG strain as shown in SEQ ID No. 1 and that extends in the N-terminal direction up to an amino acid residue between positions 233 and 120, preferably 150, more preferably 161 of the sequence of the RSV P protein as shown in SEQ ID No. 1, or b) a C-terminal fragment, homologous to the fragment defined in a), of a P protein from another human RSV strain or from a bovine RSV strain.

The fragment may, in particular, be a C-terminal fragment of the RSV P protein selected from the group consisting of PΔ120N, PΔ150N, PΔ161N, PΔ180N, PΔ200N, PΔ220N, PΔ230N and PΔ233N.

The invention also relates to a composition in which the RSV truncated P protein comprises a C-terminal fragment of the RSV P protein as described hereinbefore that comprises the last 9 C-terminal amino acids of the RSV P protein and is devoid of at least the 119, preferably the 149, more preferably the 160 N-terminal amino acids of the RSV P protein.

For example, the RSV truncated P protein comprising a C-terminal fragment of the P protein can be formed by the fusion of the last 122 N-terminal amino acids with the last 80 C-terminal amino acids of the RSV P protein; it can, for example, be formed by the sequence of amino acids 1 to 121 and 161 to 241 of the P protein of the LONG strain of human RSV as shown in SEQ ID No. 1.

According to a further embodiment, the Paramyxoviridae virus is the measles virus and said fragment of the P protein is a C-terminal fragment of the P protein that comprises at most, or consists of, the 122 C-terminal amino acids of the P protein. More specifically, said C-terminal fragment of the measles virus P protein can consist of acids 386 to 514 of the P protein (PΔ386N) of the Edmonston B strain of measles virus, as shown in SEQ ID No. 3, or be a C-terminal fragment, homologous to that defined for the Edmonston strain P protein, of a P protein from another measles virus strain.

The term “pharmaceutically acceptable carrier” refers to any solvent, dispersion medium, absorption delaying agents, etc. which do not produce a side effect, for example an allergic reaction, in humans or animals.

Advantageously, the vaccine composition according to the invention can also comprise an adjuvant. An "adjuvant" denotes a product which increases, stimulates, activates, reinforces or modulates the immune reaction at the cell or humoral level directed against a simultaneously administered antigen. Examples of conventional adjuvants include adjuvants containing bacterial antigens, such as Freund's complete adjuvant, LPS and the derivatives thereof, bacterial toxins (cholera toxin and enterotoxin) and the detoxified mutants thereof (for example LT(R192G)), oligonucleotide sequences containing CpG motifs, inorganic adjuvants such as aluminium hydroxide (Alum), calcium phosphate or potassium phosphate, oil emulsions and emulsifying agents (saponins, for example QS21), cytokines.

The vaccine compositions according to the invention impart protection from infection by a virus of the Paramyxoviridae family, i.e. a reduction in the severity of the effects of such an infection relative to a subject not immunised with the vaccine composition.

The invention also relates to the use of a vaccine composition as defined hereinbefore in a vaccination method.

The invention therefore relates to a vaccination method including at least one administration of a vaccine composition according to the invention to a subject. Preferably, the vaccination method includes a first administration of a vaccine composition to a subject and a booster administration of said vaccine composition to the same subject. The booster administrations, by re-exposing the patient to the antigen, induce a stronger secondary immune response.

The term "subject" denotes a human being or a non-human animal, for example a bird or a mammal such as a bovine, a rodent, a dog, a cat, a pig, a monkey, exposed or likely to be exposed to infection by a Paramyxoviridae virus. Preferably, a subject in the sense of the invention is a human being or a bovine.

The vaccine composition is advantageously administered in an effective amount to induce a protective or therapeutic immune response to an infection by a virus of the Paramyxoviridae family. Obviously, the dosage depends on the active principle in question, the mode of administration, the age and the condition of the subject. The amount of N-P, N-ΔPN complex or of N-protein per dose may be between 0.1 and 200 µg and preferably between 10 and 100 µg per dose of vaccine.

The vaccine composition can be administered by any route, in particular mucosally (for example, ocularly, intranasally, orally) or parenterally (for example, subcutaneously, intradermally, intramuscularly, intravenously or intraperitoneally).

Diagnostic Applications

The soluble N proteins of a virus of the Paramyxoviridae family, optionally in the form of a N protein/truncated P protein soluble complex, also form a reagent usable in diagnostic applications for the detection of antibodies directed against said N protein of the Paramyxoviridae virus.

The invention therefore also relates to a diagnostic reagent comprising an N protein of a virus of the Paramyxoviridae family, optionally in the form of a N protein/truncated P protein soluble complex, as described hereinbefore.

A diagnostic kit comprising said reagent and appropriate detection means is also within the scope of the invention.

The invention also proposes the use of an N protein of a virus of the Paramyxoviridae family according to the invention for the detection, in vitro or in vivo, of antibodies directed against said N protein.

The invention also relates to the use of a method for the detection, in a biological sample, of antibodies specifically directed against the N protein of a virus of the Paramyxoviridae family, said method including the steps consisting in:
a) contacting said biological sample with an N protein of a virus of the Paramyxoviridae family,
b) detecting the N protein/antibody complexes formed, the presence of such complexes being indicative of the presence of specific antibodies of the N protein of the virus of the Paramyxoviridae family in the biological sample.

The biological sample may be a tissue sample obtained, for example, by muscle, liver, heart, brain, etc. biopsy or a liquid sample, for example a biological liquid such as blood, plasma or cerebrospinal fluid.

The complexes can be detected by conventional means well known to a person skilled in the art such as (size exclusion, affinity, etc.) chromatography or electrophoresis under non-denaturing conditions.

In the method for the detection of antibodies specifically directed against the N protein as defined hereinbefore, the N protein contacting with the biological sample can have the form of an N protein/P protein complex.

The following examples and figures illustrate the invention without restricting its scope.

FIGURES

Figure 4:
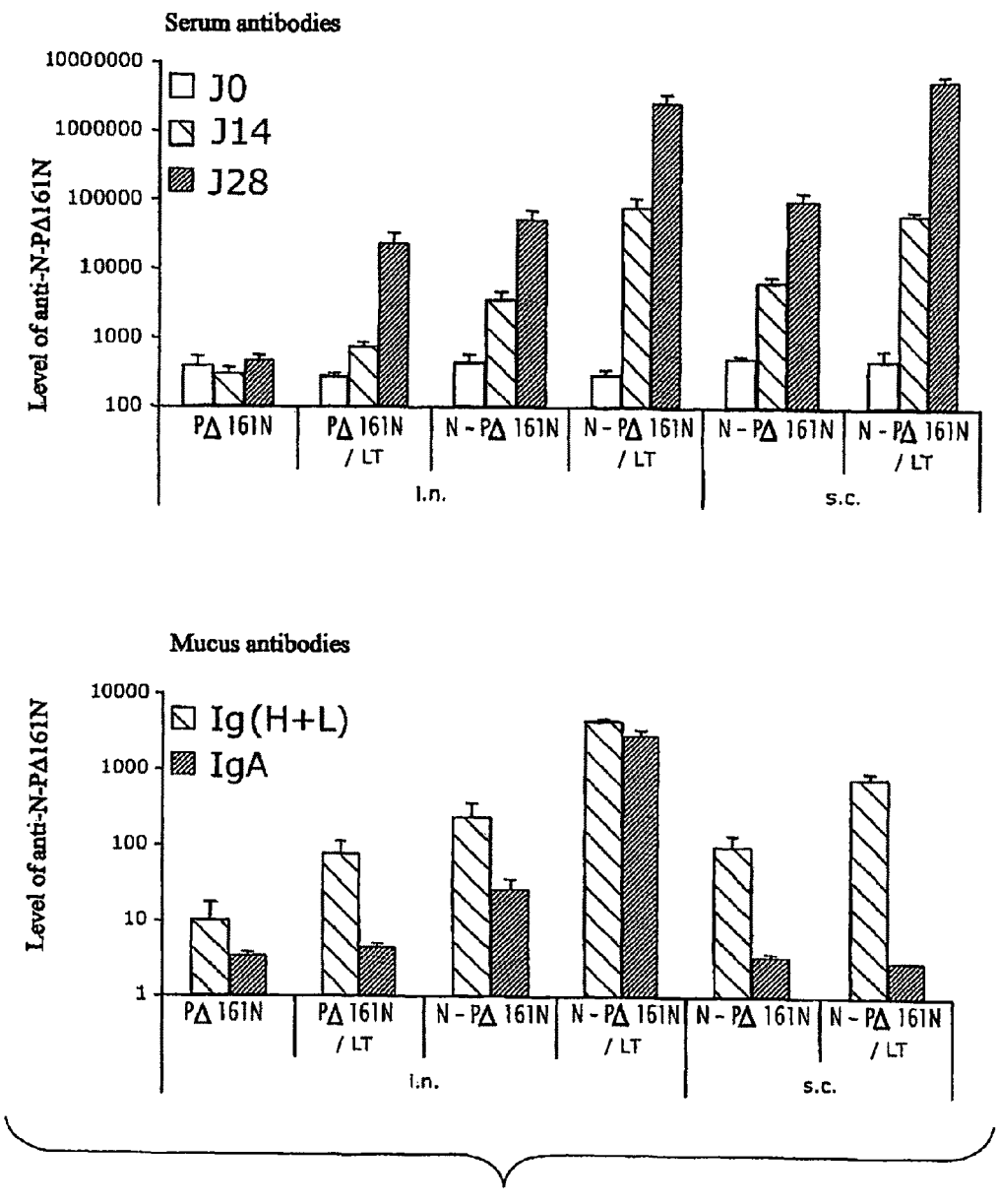

FIG. 4 describes the results of the analysis of the immunogenicity of the ring-structured N protein by measuring the production of antibodies directed against the N-PΔ161N complex. BALB/c mice were immunised intranasally (i.n.) or subcutaneously (s.c.) with 20 µg of N-PΔ161N or PΔ161N complex in the presence or absence of the mucosal adjuvant LT(R192G). A booster dose was administered after two weeks (J14). The animals were euthanised two weeks after the booster dose (J28). To measure the serum antibodies, the serum was collected at J0, J14 and J28 (A). To measure the mucus antibodies, the bronchoalveolar lavages were carried out at J28 (B). The level of antibodies against N-PΔ161N was measured by ELISA. The data was expressed as the average±standard error of mean (n=5) and represented with a logarithmic scale.

Figure 5:
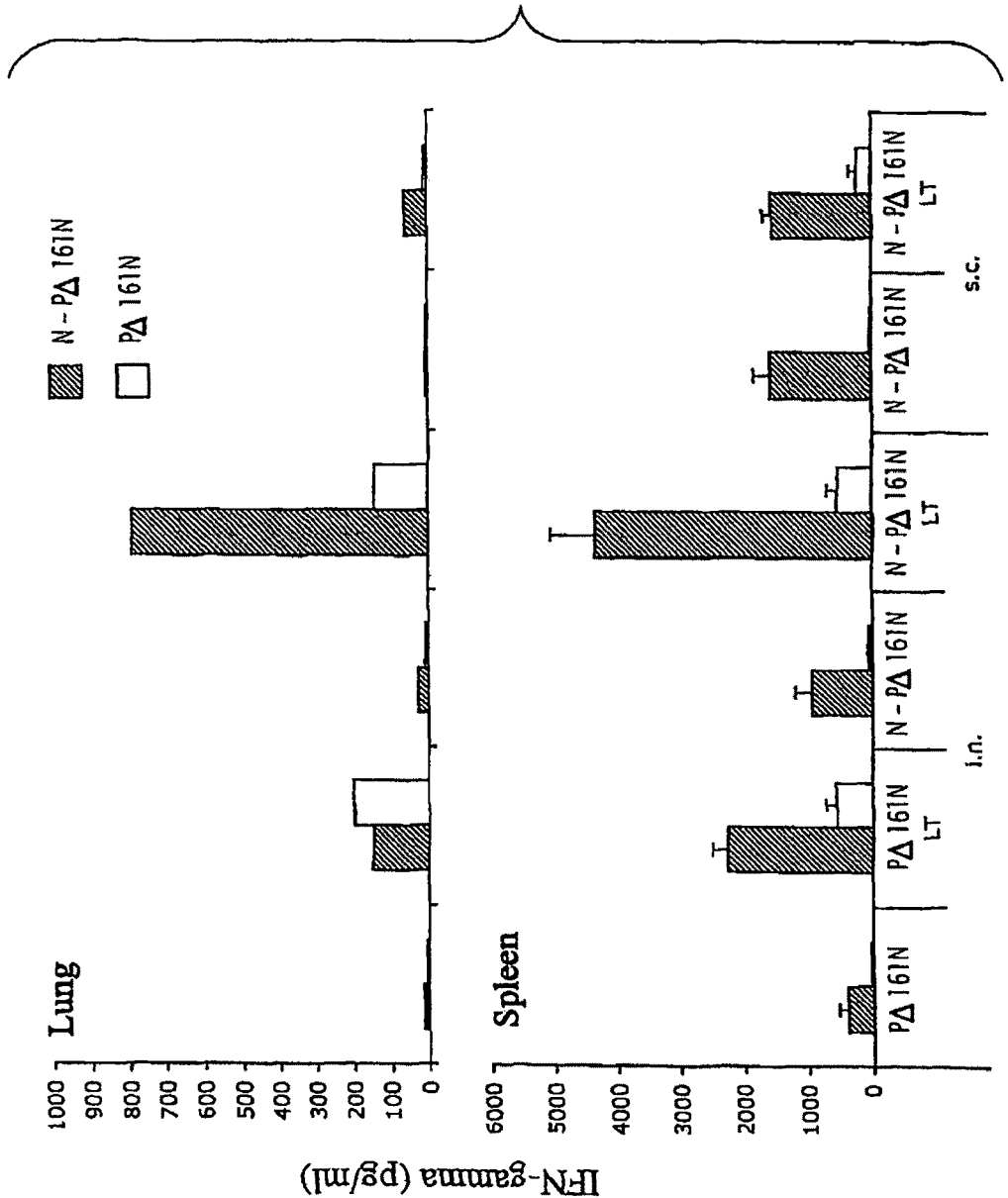

FIG. 5 describes the results of the analysis of the immunogenicity of the ring-structured N protein by measuring the PΔ161N and N-PΔ161N specific cell response. BALB/c mice were immunised intranasally (i.n.) or subcutaneously (s.c.) with 20 µg of N-PΔ161N complex or PΔ161N in the presence or absence of the mucosal adjuvant LT(R192G). A booster dose was administered after two weeks (J14). The animals were euthanised two weeks after the booster dose (J28) to remove spleens and lungs. The cells of the spleen and the lung were cultured for 72 h in the presence of N-PΔ161N, PΔ161N or without restimulation. The secretion of IFN-γ was measured by ELISA. Without restimulation, the base level of IFN-γ was less than 15 pg/ml. The data was expressed as the average±standard error of mean (n=5).

EXAMPLES

Example 1

Construction of the Plasmids Containing the C-Terminal Region of the RSV Phosphoprotein The RSV Long strain P protein is composed of 241 amino acid residues.

Sequences of the oligonucleotide primers (from 5' to 3') used to amplify the C-terminal portion of the RSV P protein (the BamHI restriction sites are underlined; the ATG start codon of the P gene is in bold face):

```
LONG-PBam+:
                                        (SEQ ID No. 11)
GAGGGATCCATCATGGAAAAGTTTGCTCCTG

LONG-P-:
                                        (SEQ ID No. 12)
CTGTTGGTGTTGTGTGTTGAAGTGCAG

P161B+:
                                        (SEQ ID No. 13)
GAGGGATCCTCTGCTAGGGATGGTATAAGAG

P180B+:
                                        (SEQ ID No. 14)
GAGGGATCCAAAATCAGAACTGAAGCATTAATGACC

P201B+:
                                        (SEQ ID No. 15)
GAGGGATCCGAGGAAAGTGAAAAGATGGCAAAAG

P221B+:
                                        (SEQ ID No. 16)
GAGGGATCCGAGAAATTGAACAACCTGTTGG

P230NB+:
                                        (SEQ ID No. 17)
GATCCAATGATAGTGACAATGATCTATCACTTGAAGATTTCTGA

P230N-:
                                        (SEQ ID No. 18)
TCAGAAATCTTCAAGTGATAGATCATTGTCACTATCATTG
```

The cDNA of the P gene of the Long strain of RSV was amplified by RT-PCR from Hep-2 cells infected with the Long strain of human RSV using the LONG-PBam+ and LONG-P− primers (Castagné et al., 2004). The PCR product was digested by the BamHI restriction enzyme and cloned in the pGEX-4T-3 plasmid (Pharmacia) at the BamHI-SmaI sites in frame with the glutathione-S-transferase or GST encoding gene. The plasmid is called pGEX-P.

Cloning of P161-241 (PΔ161N)

The C-terminal region of P (amino acids 161-241) was amplified by PCR from the pGEX-P plasmid under the following conditions:
PCR primers: P161B+ and LONG-P− 100 ng each (1 µl each)
DNA matrix pGEX-P: 10 ng (1 µl)
Enzyme: Pfu Turbo (Stratagene) (units per µl): 1 µl
dATP: 0.2 mM final
dGTP: 0.2 mM final
dCTP: 0.2 mM final
dTTP: 0.2 mM final
1×Pfu buffer final (Stratagene)
Final volume: 100 µl The PCR was carried out under the following conditions:
5 cycles: 15 seconds at 94° C., 2 minutes at 40° C., 1 minute at 72° C.;
25 cycles: 15 seconds at 94° C., 1 minute at 55° C., 1 minute at 72° C.

The amplified DNA was extracted with a volume (100 µl) of phenol/chloroform (1 vol/1 vol), then a volume of chloroform, and finally precipitated by the addition of one tenth of the volume of 5M NaCl (10 µl) and two volumes of 100% ethanol (200 µL). DNA was centrifuged for 20 minutes at 13,000 g, washed with a volume of 70% ethanol, dried, resuspended in a volume of water of 90 µl. After the addition of 10 µl of 10× BamHI enzyme buffer, the DNA was digested for 2 hours at 37° C. in the presence of 10 units of BamHI enzyme. The digested DNA was deposited on a 1.5% agarose gel in 1× Tris-Borate-EDTA buffer (TBE) in the presence of ethidium bromide and caused to migrate by electrophoresis. The band corresponding to the P161-241 DNA was cut and the DNA extracted by electroelution. The DNA was re-extracted with a volume of phenol/chloroform, a volume of chloroform and ethanol-precipitated. It was ligated with the BamHI and SmaI digested pGEX-4T-3 vector after purification in 1% agarose gel:
pGEX-4T-3 DNA: 100 ng
P161-241 DNA: 100 ng
1× ligase buffer final
Ligase (5 U/µl): 1 µl
Final volume: 20 µl The mixture was incubated overnight at 14° C. The next day, DH5-alpha TM (Life Technologies) competent bacteria were transformed with 10 µl of ligation product and spread on a Petri dish containing L-agar medium supplemented with 100 µg/ml final of ampicillin. The recombinant bacteria colonies were screened by plasmid minipreparation and digestion by the BamHI and XhoI restriction enzymes. The recombinant plasmids then showed two bands on agarose gel, one corresponding to the vector (4.9 kb) and the second corresponding to the C-terminal portion of P (246 pb). The recombinant plasmids were entirely sequenced.

Cloning of P180-241, P201-241, P221-241

The P fragments corresponding to amino acid portions 180-241, 200-241, 220-241 were obtained by PCR from the pGEX-P plasmid using the following primers:
P180-241: primers P180B+ and LONG-P
P200-241: primers P201B+ and LONG-P−
P220-241: primers P221B+ and LONG-P−

They were amplified and cloned in the same way as P161-241 (see above).

Cloning of the Gene Encoding the Nucleocapsid Protein of the RSV Long Strain

The gene encoding the N protein of the Long strain of human RSV was obtained by RT-PCR from virus-infected Hep-2 cells. The primers used were:

```
                                        (SEQ ID No. 19)
LONG-Nbam+:  GAGGGATCCATGGCTCTTAGCAAAGTCAAGTTG (SEQ ID No. 20)
LONG-N-      TTAACTCAAAGCTCTACATCATTATCTTTTGG
```

The PCR products were digested by BamHI and cloned in the pGEX-4T-3 plasmid at the BamHI-SmaI sites. The N-encoding region (SEQ ID No.) was subcloned by digestion of the pGEX-N plasmid by BamHI-XhoI and subcloned in the pET28a+ plasmid (Novagen; SEQ ID No. and see Figure).

Cloning of P231-241

The following primers were denatured by heating to 94° C., for 5 minutes, and cooled to room temperature:

P231NB+ GATCCGATAGTGACAATGATCTATCACTTGAAGATTTCTGA (SEQ ID No. 21)

P231N-  TCAGAAATCTTCAAGTGATAGATCATTGTCACTATCG (SEQ ID No. 22)

After hybridization, 10 ng of double-stranded oligonucleotides were ligated with 100 ng of pGEX-4T-3 plasmid DNA digested by the BamHI and SmaI enzymes and purified by agarose gel electrophoresis. The recombinant plasmids were checked by sequencing at the level of the N gene.

Example 2

Expression and Purification of the Complexes

The BL21 (DE3) (Novagen) competent bacteria were transformed with 1 µg of pGEX-PΔ DNA and 1 µg of pET-N DNA, then spread on a Petri dish containing L-agar medium supplemented with 100 µg/ml final of ampicillin and 50 µg/ml final of kanamycin. A colony was picked and cultivated overnight at 37° C. in 2 ml of LB medium containing 100 µg/ml of ampicillin and 50 µg/ml of kanamycin. The next morning, 1 ml of saturated culture was used to pitch 1 litre of LB medium supplemented with antibiotics and cultivated until the evening. In the evening, a volume of fresh LB medium containing IPTG (which induces the expression of the proteins) at a concentration of 160 µg/ml was added to the culture and the mixture was cultivated overnight at 28° C. The next day, the bacteria were centrifuged for 15 minutes at 5,000 rpm and the pellet was resuspended in 100 ml of the following buffer:
50 mM Tris (pH 7.8)
60 mM NaCl
2 mM DTT
1 mM EDTA
4 mM benzamidine
1× antiproteases (complete EDTA-free protease inhibitor cocktail, ref. Roche No. 11 873 580 001), i.e one tablet for 50 ml of lysis buffer
0.1% Triton-X100

10 ml of the same buffer supplemented with lysozyme at 10 mg/ml (1 mg/ml final) were added. The bacteria were incubated for 1 hour on ice (lysis). When the mixture became viscous, it was sonicated on ice 3 times for 1 minute using a probe immersed in the mixture, a 5-minute interval being left between each sonication. The mixture was centrifuged for 30 minutes at 10,000 g at 4° C., then the supernatant was recovered. The supernatant was recentrifuged for 30 minutes at 10,000 g at 4° C., then the new supernatant was recovered. 4 ml of glutathione-sepharose 4B beads (Amersham-Pharmacia) were washed while taking 8 ml of bead/buffer mixture (vol/vol) with the lysis buffer. The beads were left in an equivalent volume of buffer, added to the clarified bacterial lysate and agitated at 4° C. overnight. The next day, the beads were centrifuged at 2,000 rpm for 3 minutes; then the supernatant was removed and the beads washed three times with the lysis buffer without antiproteases, three times in 1×PBS buffer.

The beads were cleaved at the thrombin site using biotinylated thrombin (Novagen) in a proportion of 1 µl (1 U) of thrombin (thrombin cleavage capture kit, No. 69022-3FRZ) to 1 ml of beads. The beads were incubated overnight at 20° C. and, the next day, centrifuged for 3 minutes at 2,000 rpm and left to decant for 15 minutes to recover the supernatant. An equivalent volume of 1× PBS was added to the beads; the mixture was stirred and left to decant. The supernatant was recovered again and added to the previously recovered supernatant. Added to the recovered supernatant were beads of streptavidin agarose (Novagen ref. 69203) in a proportion of 16 µl of resin (i.e. 32 µl of resin/buffer mixture (vol/vol)). The mixture was agitated for one hour, then centrifuged for 3 minutes at 2,000 rpm and the supernatant was recovered. A protein concentration of 2 mg/ml was obtained.

10 µl of the supernatant containing the cleavage products were denatured in 1× Laemmli buffer, boiled and deposited on a 12% polyacrylamide gel in 0.1% SDS Tris-Glycine buffer, then stained with Coomassie blue after electrophoresis to display the proteins.

Example 3

Separation of N and PΔ161N (P161-241) and Purification of the N Rings

Figure 1:
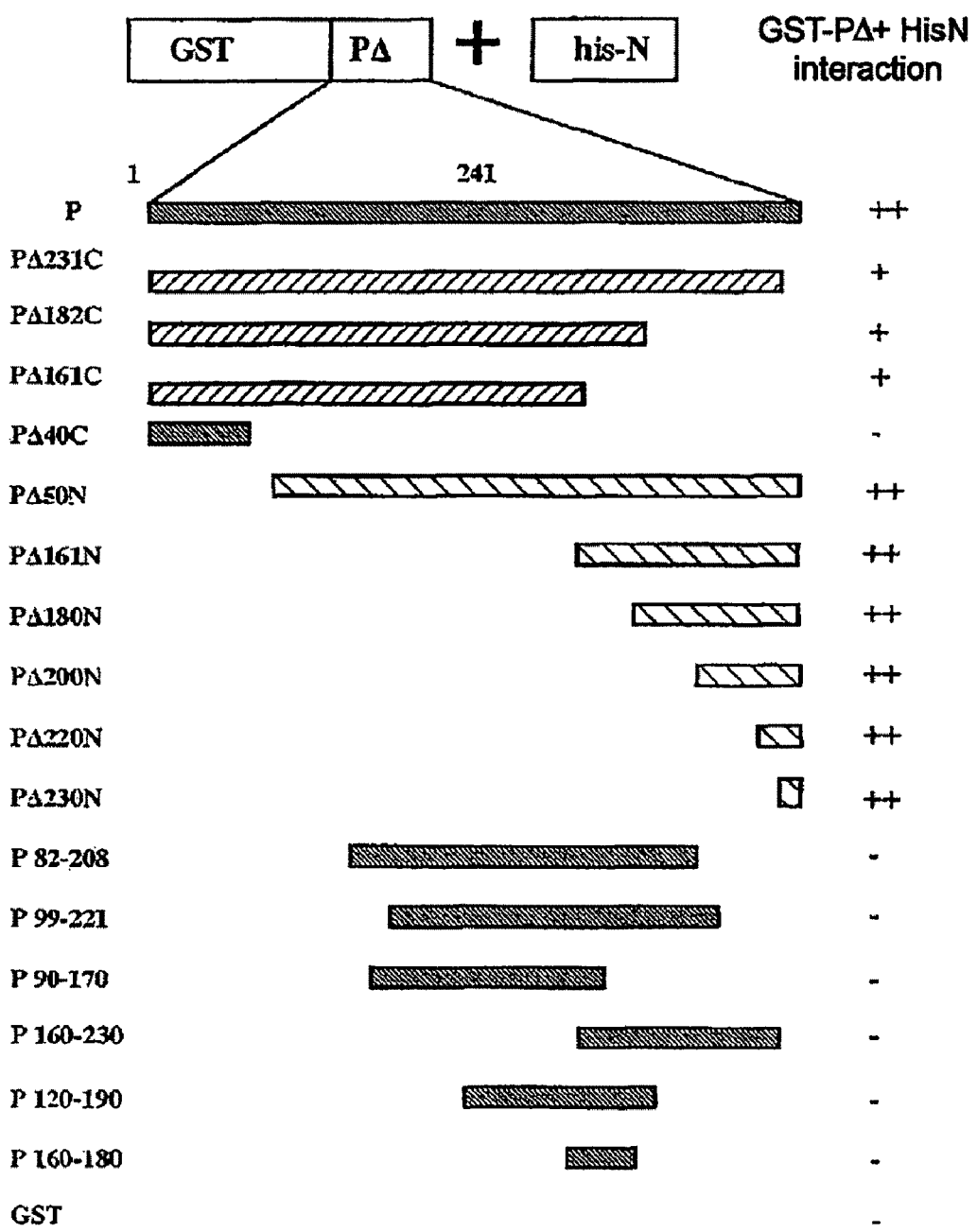
FIG. 1 shows the mapping of the P-N interaction domain on P. The P protein has been fused to GST and coexpressed in *E. coli* with the N protein expressed on another plasmid.
Figure 2:
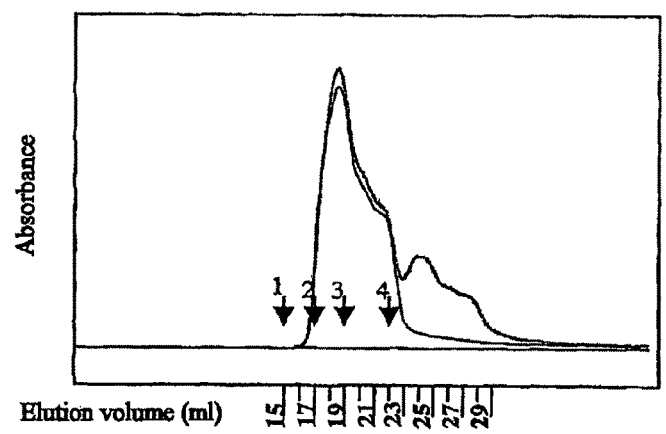
FIG. 2 shows the elution profile of the N-PΔ161N complexes in size exclusion chromatography. (A) Elution profile at 220 nm in a TSK column. (B) Analysis by acrylamide gel electrophoresis of the various fractions after Coomassie blue staining. Fractions 17 to 22 contain merely N-RNA rings.
Figure 2:
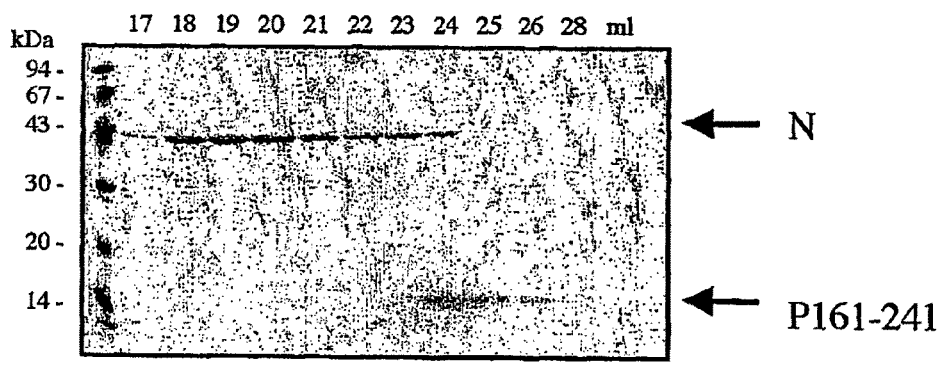

The proteins present in the supernatant could be separated by size exclusion chromatography (gel filtration, FIG. 2) in 1× PBS. The N protein was excluded at an apparent size of 450,000 Da and PΔ161N with a mass of 15 kDa.

Figure 3:
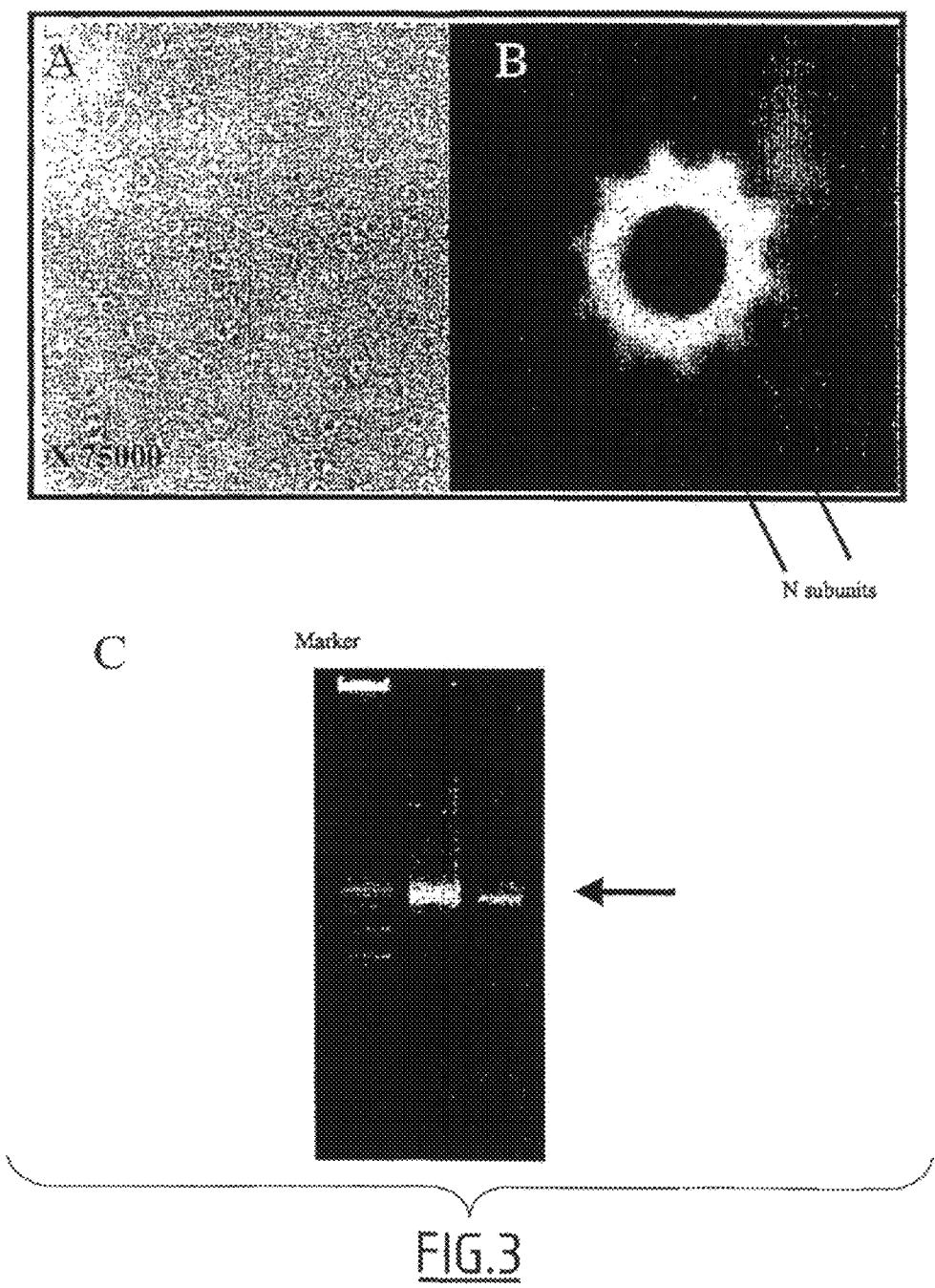
FIG. 3 shows the structure of the RSV N protein rings. (A) Electron microscope analysis of the N-RNA rings purified by P161-241. (B) Cryomicroscopy reconstruction. (C) Agarose gel analysis of the RNA present in the rings.

Electron microscope observation of the "N" fraction from the size exclusion chromatography showed that the N protein formed rings (FIG. 3A) having a diameter of 7 nm and containing 10 N subunits (FIG. 3B). The rings contained an RNA of approximately 70 pb (FIG. 3c).

Example 4

Evaluation of the Immunogenic Properties of the Ring-Structured Recombinant N Protein A Nasal or Subcutaneous Vaccination was Carried Out in Mice, in the Presence or Absence of Adjuvant:
Mice: 30 10-12 week-old female BALB/c mice, bred at the Unité Expérimentale Animalerie Rongeur (INRA, Jouyen-Josas).
Antigens: P161-241 and {P161-241+N} complex soluble at a concentration of 1 mg/ml after separation from GST by thrombin cleavage and elimination of the biotinylated thrombin by streptavidin coupled beads.
Adjuvant: E. coli LT(R192G) lymphotoxin, 1 mg/ml (Choi et al., 2004).
Samples
at J0, J14 and J28, blood sampling from the retro-orbital sinus
at J28:
bronchoalveolar lavage (BAL) with 1.5 ml of HBSS and 1 mM EDTA medium
dissection of the spleen and the lung in RMPI medium supplemented with antibiotics (penicillin 100 UI/ml and streptomycin 100 µg/ml, PS), on ice
Experimental Design:

| Groups (5 mice) | Treatments | J0 primary injection | J14 booster dose | J28 autopsy |
|---|---|---|---|---|
| 1 | Intranasal | P161-241 | P161-241 | Serum |
| 2 | 20 µg of proteins ± 10 µg of LT(R192G), in a | P161-241 LT(R192G) | P161-241 LT(R192G) | BAL Spleen |
| 3 | | P161-241 + N | P161-241 + N | Lung |

-continued

| Groups (5 mice) | Treatments | J0 primary injection | J14 booster dose | J28 autopsy |
|---|---|---|---|---|
| 4 | volume of 50 µl | P161-241 + N LT(R192G) | P161-241 + N LT(R192G) | 5 |
| 5 | Subcutaneous | P161-241 + N LT(R192G) | P161-241 + N LT(R192G) | |
| 6 | 20 µg of proteins ± 10 µg of LT(R192G), in a volume of 50 µl | P161-241 + N LT(R192G) | P161-241 + N LT(R192G) | |

Production of Anti-N Antibodies

The sera were collected from blood samples (1 night of exudation at 4° C.) then frozen at −20° C.

The BALs were centrifuged for 5 min at 1,700 rpm; the supernatants were collected (approximately 1 ml) and frozen at −20° C.

The anti-N antibodies (total Ig, IgG1, IgG2a and IgA) were searched for in the sera and the BALs by E.L.I.S.A.: 96-well plates (Immulon 2HB, ThermoLabsystems) were sensitised overnight at 4° C. with the P161-241+N complex (200 ng per well) in 0.1 M bicarbonate buffer (pH 9.5). The plates were washed 5 times with 200 µl per well of PBS 0.05% Tween 20 (use of a Wellwash machine, Labsystems). The plates were then saturated for 1 h at 37° C. with 150 µl per well of 0.05% Tween 20/PBS buffer and 5% foetal calf serum (PBS-T-FCS). After 5 washes, the samples to be titrated were diluted in PBS-T-FCS (seven successive three-fold dilutions starting from a first dilution of 1/30 for the sera and to one third for the BALs). The plates were incubated for 2 h at 37° C. After 5 washes, the secondary antibody diluted in PBS-T-FCS was distributed in a proportion of 100 µl per well. The secondary antibodies used were conjugated to peroxidase and directed against mouse immunoglobulins: total IgG (1/4000, P.A.R.I.S.), IgG1 (1/2000, BD biosciences), IgG2a (2,000$^{th}$, BD biosciences) or IgA (1/1000, Caltag). The plates were incubated for 2 h at 37° C. and washed 5 times. The plates were then incubated with the substrate of the peroxidase (TMB, 100 µl per well) for 10 min in the dark. The enzymatic reaction was stopped by the addition of 50 µl of 2M $H_3PO_4$. The optical densities (OD) were read at 450 nm (Dynex reader). The curve $OD_{450}$=f (dilution) was modelled by the regression curve y=(b+cx)/(1+ax). The titre of antibodies was determined as the dilution value giving twice the $OD_{450}$ of a control sample (J0) when most diluted.

Production of IFN-γ by P161-241 and N Specific T Lymphocytes

The removed spleens and lungs were treated according to the same protocol. The spleens were treated individually and the lungs were grouped into experimental batches (5 lungs per batch).

The tissues were sliced then gently ground on a filter (100 µm cell strainer, BD Falcon) in RPMI and PS medium. The cell suspension was centrifuged at 1,700 rpm for 10 min at 4° C.

The cells were resuspended in 1 ml of erythrocyte lysis buffer (hypotonic saline buffer) and incubated for 5 min at room temperature. The lysis reaction was stopped by the addition of 10 ml of complete RPMI (PS, 2 mM L-glutamine and 10% FCS). The membrane debris were decanted and the cells were washed three times by centrifugation (1,700 rpm for 10 min at 4° C.). The cell suspensions were counted on a Malassez cell.

The cells were cultured in culture-treated 96-well microplates (Falcon) in a proportion of 200,000 cells per well in 200 µl of complete RPMI medium.

Four culture conditions were tested in triplicate for each cell suspension:
PMA (phorbol 12-myristate 13-acetate, Sigma) 10 ng/ml and ionomycin (Sigma) 1 µg/ml (positive control, polyclonal activation)
complete RPMI (negative control)
P161-241 10 µg/ml
P161-241+N 10 µg/ml After 72 h of culture at 37° C. with 5% $CO_2$, the culture supernatants were collected and frozen at −20° C. until titration of the IFN-γ by ELISA.

IFN-γ ELISA: 96-well plates (Immulon 2HB, ThermoLabsystems) were sensitised overnight at 4° C. with the mouse anti-IFN-γ capture antibody (BD Bioscience) at 4 µg/ml in 0.1 M bicarbonate buffer (pH 9.5) (100 µl/well). The plates were washed 5 times with 200 µl per well of PBS 0.05% Tween 20 (use of a Wellwash machine, Labsystems). The plates were then saturated for 2 h at 37° C. with 150 µl per well of PBS 0.05% Tween 20 buffer and 2% bovine serum albumin (PBS-T-BSA). After 5 washes, the mouse recombinant IFN-γ standard (R&D systems) and the samples to be titrated were diluted in PBS-T-BSA by successive half-dilutions. The IFN-γ range was diluted from 3312.5 pg/ml to 3.235 pg/ml. Four successive half-dilutions were carried out on the pure samples. The plate was then incubated overnight at 4° C. After 5 washes, the biotinylated detection antibody (BD Biosciences) was distributed (1 µg/ml in PBS-T-BSA, 100 µl/well) and incubated for 3 h at 4° C. After 5 washes, the streptavidin-peroxidase conjugate (Pierce) was distributed (1 µg/ml in PBS-T-BSA, 100 µl/well) and incubated for 1 h at 4° C. After 5 washes, the substrate of the peroxidase (ABTS+ $H_2O_2$) was distributed in the wells. After 45 minutes of incubation, the optical densities were read at 405 nm (ELISA Dynex reader). The IFN-γ concentration of the samples was calculated relative to the IFN-γ range.

REFERENCES

Ames, T. R. 1993. The epidemiology of BRSV infection. Vet. Med. 881-884.

Bhella, D., Ralph, A., Murphy L. B., & Yeo, R. P. 2002. Significant differences in nucleocapsid morphology within the Paramyxoviridae. Journal of General Virology; 83, 1831-1839.

Castagné, N., A. Barbier, J. Bernard, H. Rezaei, J.-C. Huet, C. Henry, B. Da Costa, and J.-F. Eléouët. 2004. Biochemical characterization of the Respiratory Syncytial Virus P-P and P-N protein complexes and localization of the P protein oligomerization domain. Journal of General Virology; 85: 1643-1653.

Choi et al., 2004, Protein Expression and Purification; 38, pp 205

Elvander, M. 1996. Severe respiratory disease in dairy cows caused by infection with bovine respiratory syncytial virus. Vet. Rec.; 138, 101-105.

Freytag, L C et Clements, J D. 2005. Mucosal adjuvants. Vaccine.; 23(15):1804-13.

Gaddum, R. M., R. S. Cook, J. M. Furze, S. A. Ellis & G. Taylor. 2003. Recognition of bovine respiratory syncytial virus proteins by bovine CD8a T lymphocytes. Immunology; 108, 220-229;

Goulder P J, Lechner F, Klenerman P, McIntosh K, Walker B D. 2000. Characterization of a novel respiratory syncytial virus-specific human cytotoxic T-lymphocyte epitope. J Virol.; 74(16):7694-7.

Johansson et al., 2003; Journal of Biological Chemistry vol. 278 p 44567-44573.

Khattar S K, Yunus A S, Samal S K. 2001a. Mapping the domains on the phosphoprotein of bovine respiratory syncytial virus required for N-P and P-L interactions using a minigenome system. J Gen Virol.; 82(Pt 4):775-9.

Khattar S K, Yunus A S, Collins P L, Samal S K. 2001b. Deletion and substitution analysis defines regions and residues within the phosphoprotein of bovine respiratory syncytial virus that affect transcription, RNA replication, and interaction with the nucleoprotein. Virology.; 285(2):253-69.

Kolakofsky D, Le Mercier P, Iseni F, Garcin D. 2004. Viral DNA polymerase scanning and the gymnastics of Sendai virus RNA synthesis. Virology.; 318(2):463-73. Review.

Maggon K, Barik S. 2004. New drugs and treatment for respiratory syncytial virus. Rev Med Virol. 14(3):149-68. Review.

Mallipeddi S K, Lupiani B, Samal S K. 1996. Mapping the domains on the phosphoprotein of bovine respiratory syncytial virus required for N-P interaction using a two-hybrid system. J Gen Virol.; 77 (Pt 5):1019-23.

Martinez X, Li X, Kovarik J, Klein M, Lambert P H, Siegrist C A. 1999. Combining DNA and protein vaccines for early life immunization against respiratory syncytial virus in mice. Eur J Immunol.; 29(10):3390-400.

Mavrakis M, Iseni F, Mazza C, Schoehn G, Ebel C, Gentzel M, Franz T, Ruigrok R W. 2003. Isolation and characterisation of the rabies virus N°-P complex produced in insect cells. Virology.; 305(2):406-14.

McNeal M M, VanCott J L, Choi A H, Basu M, Flint J A, Stone S C, Clements J D, Ward R L. 2002. CD4 T cells are the only lymphocytes needed to protect mice against rotavirus shedding after intranasal immunization with a chimeric VP6 protein and the adjuvant LT(R192G). J Virol.; 76(2):560-8.

Meric C, Spehner D, Mazarin V. 1994. Respiratory syncytial virus nucleocapsid protein (N) expressed in insect cells forms nucleocapsid-like structures. Virus Res. 31(2):187-201.

Perrin, B., Dannacher, G., et Solsona, M. 1979. Mise en évidence des anticorps contre le virus respiratoire syncytial chez les bovins français. Rec. Med. Vet. 155, 465-471.

Samal S K, Pastey M K, McPhillips T H, Mohanty S B. 1993. Bovine respiratory syncytial virus nucleocapsid protein expressed in insect cells specifically interacts with the phosphoprotein and the M2 protein. Virology.; 193(1):470-3.

Slack M S, Easton A J. 1998. Characterization of the interaction of the human respiratory syncytial virus phosphoprotein and nucleocapsid protein using the two-hybrid system. Virus Res.; 55(2):167-76.

Sparer T E, Matthews S, Hussell T, Rae A J, Garcia-Barreno B, Melero J A, Openshaw P J. 1998. Eliminating a region of respiratory syncytial virus attachment protein allows induction of protective immunity without vaccine-enhanced lung eosinophilia. J Exp Med; 187 (11): 1921-6.

Tarbouriech, N., Curran, J., Ruigrok, R. W., & Burmeister, W. P. (2000). Tetrameric coiled coil domain of Sendai virus phosphoprotein. Nature Structural Biology 7, 777-781.

Taylor G, Bruce C, Barbet A F, Wyld S G, Thomas L H. 2005. DNA vaccination against respiratory syncytial virus in young calves. Vaccine; 23(10):1242-50

Taylor, G. L. H. Thomas, J. M. Furze, R. S. Cook, S. G. Wyld, R. Lerch, R. Hardy and G. W. Wertz. 1997. Recombinant vaccinia viruses expressing the F, G or N, but not the M2, protein of bovine respiratory syncytial virus (BRSV) induce resistance to BRSV challenge in the calf and protect against the development of pneumonic lesions. Journal of General Virology; 78, 3195-3206.

Thompson W. W., D. K. Shay, E. Weintraub, L. Brammer, N. Cox, L. J. Anderson, K. Fukuda. 2003. Mortality associated with influenza and respiratory syncytial virus in the United States. JAMA.; 289(2):179-86.

Wellemans, G., and J. Leunen. 1975. Le virus respiratoire syncytial et les troubles respiratoires des bovins. Ann. Med. Vet.; 119, 359-369.

---

The invention claimed is:

1. A method of preparing a soluble N protein/truncated P protein complex of a virus of the family Paramyxoviridae, said method comprising the steps of:

a) coexpressing an N protein of a virus of the family Paramyxoviridae with a truncated P protein of the same virus of the family Paramyxoviridae, said truncated P protein being devoid of the P oligomerisation domain and being capable of interacting with the N protein; and b) collecting the soluble N protein/truncated P protein complexes thus formed;

wherein the virus of the family Paramyxoviridae is a Respirovirus, a Morbillivirus, a *Pneumovirus*, or a parainfluenza virus.

2. The method according to claim 1, wherein the virus of the family Paramyxoviridae is a *Pneumovirus*.

3. The method according to claim 1, wherein the Paramyxoviridae virus is bovine or human respiratory syncytial virus (RSV).

4. The method according to claim 3, wherein said truncated P protein is a C-terminal fragment of the P protein that comprises the last 9 C-terminal amino acids of the P protein of the RSV and that lacks at least the 160 N-terminal amino acids of the P protein of RSV.

5. The method according to claim 4, wherein said truncated P protein which is devoid of the P oligomerisation domain and is capable of interacting with the N protein is:

a) a C-terminal fragment of the P protein of RSV that consists of the sequence of amino acids 161 to 241 of the P protein of the LONG strain of human RSV as shown in SEQ ID NO. 1, or a fragment thereof that comprises the sequence of amino acids 233 to 241 of the P protein of the LONG strain of human RSV as shown in SEQ ID NO. 1, or b) a C-terminal fragment of a P protein from another strain of human RSV or from a strain of bovine RSV that corresponds to the fragment defined in a) without any other modifications, said C-terminal fragment of a P protein from another strain of human RSV or from a strain of bovine RSV being capable of interacting with the N protein and being devoid of the P oligomerisation domain.

6. The method according to claim 1, wherein said P protein is expressed in the form of a fusion protein with a label protein.

7. The method according to claim 1, wherein said N protein and said truncated P protein are coexpressed in a bacterial expression system.

8. The method according to claim 1, wherein the virus of the family Paramyxoviridae is a Paramyxovirinae or a Pneumovirinae.

9. The method according to claim 1, wherein the virus of the family Paramyxoviridae is selected from the group consisting of the measles virus and the parainfluenza virus.

10. The method according to claim 4, wherein said truncated P protein is a C-terminal fragment of the P protein of RSV that consists of the sequence of amino acids 161 to 241 of the P protein of the LONG strain of human RSV as shown in SEQ ID NO. 1.

11. The method according to claim 4, wherein said truncated P protein is a C-terminal fragment of the P protein of RSV that consists of the sequence of amino acids 233 to 241 of the P protein of the LONG strain of human RSV as shown in SEQ ID NO. 1.

12. The method according to claim 3, wherein said truncated P protein is a C-terminal fragment of the P protein that comprises the last 9C-terminal amino acids of the P protein of the RSV and that lacks at least the 119 N-terminal amino acids of the P protein of RSV.

13. The method according to claim 3, wherein said truncated P protein is a C-terminal fragment of the P protein that comprises the last 9C-terminal amino acids of the P protein of the RSV and that lacks at least the 149 N-terminal amino acids of the P protein of RSV.

14. The method according to claim 3, wherein said truncated P protein is a C-terminal fragment of the P protein that is selected from the group consisting of amino acids 120 to 241 of the P protein of the LONG strain of human RSV as shown in SEQ ID NO. 1, amino acids 150 to 241 of the P protein of the LONG strain of human RSV as shown in SEQ ID NO. 1, amino acids 161 to 241 of the P protein of the LONG strain of human RSV as shown in SEQ ID NO. 1, amino acids 180 to 241 of the P protein of the LONG strain of human RSV as shown in SEQ ID NO. 1, amino acids 200 to 241 of the P protein of the LONG strain of human RSV as shown in SEQ ID NO. 1, amino acids 220 to 241 of the P protein of the LONG strain of human RSV as shown in SEQ ID NO. 1, amino acids 230 to 241 of the P protein of the LONG strain of human RSV as shown in SEQ ID No. 1 and amino acids 233 to 241 of the P protein of the LONG strain of human RSV as shown in SEQ ID NO. 1.

15. The method according to claim 1, wherein the Paramyxoviridae virus is measles virus.

16. The method according to claim 15, wherein said truncated P protein is a C-terminal fragment of the measles virus P protein comprising at most the 122 C-terminal amino acids of the P protein.

17. The method according to claim 15, wherein said truncated P protein which is devoid of the P oligomerisation domain and is capable of interacting with the N protein is:

a) a C-terminal fragment of the measles virus P protein consisting of amino acid residues 386 to 507 of the P protein of the measles virus Edmonston B strain as shown in SEQ ID NO. 3 or b) a C-terminal fragment of a P protein from another measles virus strain that corresponds to the fragment defined for the Edmonston strain P protein without any other modifications, said C-terminal fragment of a P protein from another measles virus strain being capable of interacting with the N protein and being devoid of the P oligomerisation domain.

18. The method according to claim 1, wherein said P protein is expressed in the form of a fusion protein with a protein facilitating purification of the N protein/truncated P protein complexes.

19. The method according to claim 18, wherein said protein facilitating purification of the N protein/truncated P protein complexes is a protein which can be used in affinity chromatography.

20. The method according to claim 6, wherein the label protein can be removed by enzymatic cleavage.

21. A method of preparing a soluble N protein/truncated P protein complex of a virus of the family Paramyxoviridae, said method comprising the steps of:
   a) coexpressing an N protein of a virus of the family Paramyxoviridae with a truncated P protein of the same virus of the family Paramyxoviridae, said truncated P protein being devoid of the P oligomerisation domain and being capable of interacting with the N protein; and
   b) collecting the soluble N protein/truncated P protein complexes thus formed; wherein the Paramyxoviridae virus is bovine or human respiratory syncytial virus (RSV), and wherein said truncated P protein which is devoid of the P oligomerisation domain and is capable of interacting with the N protein is a C-terminal fragment of the P protein of RSV that consists of the sequence of amino acids 161 to 241 of the P protein of the LONG strain of human RSV as shown in SEQ ID NO:1, or a fragment thereof that comprises the sequence of amino acids 233 to 241 of the P protein of the LONG strain of human RSV as shown in SEQ ID NO:1.

22. A method of preparing a soluble N protein/truncated P protein complex of a virus of the family Paramyxoviridae, said method comprising the steps of:
   a) coexpressing an N protein of a virus of the family Paramyxoviridae with a truncated P protein of the same virus of the family Paramyxoviridae, said truncated P protein being devoid of the P oligomerisation domain and being capable of interacting with the N protein; and
   b) collecting the soluble N protein/truncated P protein complexes thus formed; wherein the Paramyxoviridae virus is measles virus and wherein said truncated P protein which is devoid of the P oligomerisation domain and is capable of interacting with the N protein is a C-terminal fragment of the measles virus P protein consisting of amino acid residues 386 to 507 of the P protein of the measles virus Edmonston B strain as shown in SEQ ID NO:3.

* * * * *